United States Patent
Amb et al.

(10) Patent No.: US 9,006,376 B2
(45) Date of Patent: Apr. 14, 2015

(54) GERMOLE CONTAINING CONJUGATED MOLECULES AND POLYMERS

(75) Inventors: Chad Martin Amb, Midland, MI (US); Franky So, Gainesville, FL (US); John R. Reynolds, Dunwoody, GA (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 0 days.

(21) Appl. No.: 14/001,787

(22) PCT Filed: Feb. 27, 2012

(86) PCT No.: PCT/US2012/026706
§ 371 (c)(1),
(2), (4) Date: Aug. 27, 2013

(87) PCT Pub. No.: WO2012/118728
PCT Pub. Date: Sep. 7, 2012

(65) Prior Publication Data
US 2013/0334520 A1    Dec. 19, 2013

Related U.S. Application Data

(60) Provisional application No. 61/447,392, filed on Feb. 28, 2011.

(51) Int. Cl.
*C08G 18/77* (2006.01)
*H01L 51/00* (2006.01)
*C07F 7/30* (2006.01)
*C08G 61/12* (2006.01)

(52) U.S. Cl.
CPC ........ *H01L 51/0036* (2013.01); *H01L 51/0043* (2013.01); *H01L 51/0071* (2013.01); *C07F 7/30* (2013.01); *C08G 61/123* (2013.01); *C08G 61/126* (2013.01); *C08G 2261/124* (2013.01); *C08G 2261/3243* (2013.01); *C08G 2261/344* (2013.01); *C08G 2261/414* (2013.01); *C08G 2261/91* (2013.01); *Y02E 10/52* (2013.01); *Y02E 10/542* (2013.01); *Y02E 10/549* (2013.01)

(58) Field of Classification Search
USPC .................................... 528/73, 377, 380, 370
See application file for complete search history.

(56) References Cited

U.S. PATENT DOCUMENTS

2008/0087324 A1    4/2008    Gaudiana et al.
2009/0137059 A1*   5/2009    Trogler et al. ................. 436/172

(Continued)

FOREIGN PATENT DOCUMENTS

WO    WO-2009-115413    9/2009

OTHER PUBLICATIONS

Allard, N. et al., "Germafluorenes: New Heterocycles for Plastic Electronics," *Macromolecules*, 2010, pp. 2328-2333, vol. 43.

(Continued)

*Primary Examiner* — Shane Fang
(74) *Attorney, Agent, or Firm* — Saliwanchik, Lloyd & Eisenschenk

(57) ABSTRACT

Embodiments of the invention are directed to Ge comprising heterocyclic compounds which can be used for the preparation of homopolymers and copolymers. The copolymers can be donor-acceptor (DA) alternating copolymers where the donor unit is a Ge comprising heterocyclic unit. The polymers can be used as materials in solar cells and other photovoltaic devices, transistors, diodes, light emitting devices (LEDs), conductors, supercapacitors, batteries, and electrochromic devices.

13 Claims, 3 Drawing Sheets where X = CR'$_2$, SiR'$_2$, NR', PR', POR', O, S, SO, SO$_2$, Se, SeO, SeO$_2$, Te, TeO, TeO$_2$
Y = CR', N, P

(56) References Cited

U.S. PATENT DOCUMENTS

2010/0224252 A1     9/2010    Scharber et al.
2011/0017956 A1     1/2011    Hou et al.

OTHER PUBLICATIONS

Amb, C.M. et al., "Dithienogermole as a Fused Electron Donor in Bulk Heterojunction Solar Cells," *Journal of the American Chemical Society*, 2011, pp. 10062-10065, vol. 133.

Beaujuge, P.M. et al., "Tailoring Structure—Property Relationships in Dithienosilole-Benzothiadiazole Donor-Acceptor Copolymers," *Journal of the American Chemical Society*, 2009, pp. 7514-7515, vol. 131.

Beaujuge, P.M. et al., "Spectral Engineering in π-Conjugated Polymers with Intramolecular Donor-Acceptor Interactions," *Accounts of Chemical Research*, Nov. 2010, pp. 1396-1407, vol. 43, No. 11.

Chen, H-Y. et al., "Silicon Atom Substitution Enhances Interchain Packing in a Thiophene-Based Polymer System," *Advanced Materials*, 2010, pp. 371-375, vol. 22.

Gendron, D. et al., "Synthesis and Photovoltaic Properties of Poly(dithieno[3,2-b:2'3'-d]-germole) Derivatives," *Macromolecules*, 2011, pp. 7188-7193, vol. 44.

Lee, J.K. et al. "Processing Additives for Improved Efficiency from Bulk Heterojunction Solar Cells," *J. Am. Chem. Soc.*, 2008, pp. 3619-3623, vol. 130.

Morana, M. et al., "Nanomorphology and Charge Generation in Bulk Heterojunctions Based on Low-Bandgap Dithophene Polymers with Different Bridging Atoms," *Advanced Functional Materials*, 2010, pp. 1180-1188, vol. 20.

Scharber, M. C. et al., "Influence of the Bridging Atom on the Performance of a Low-Bandgap Bulk Heterojunction Solar Cell," *Advanced Materials*, 2010, pp. 367-370, vol. 22.

Tsao, H.N. et al., "The Influence of Morphology on High-Performance Polymer Field-Effect Transistors," *Advanced Materials*, 2009, pp. 209-212, vol. 21.

Yabusaki, Y. et al., Versatile Synthesis of Blue Luminescent Siloles and Germoles and Hydrogen-Bond-Assisted Color Alteration, *Chem. Eur. J.*, 2010, pp. 5581-5585, vol. 16.

\* cited by examiner where X = CR'$_2$, SiR'$_2$, NR', PR', POR', O, S, SO, SO$_2$, Se, SeO, SeO$_2$ Te, TeO, TeO$_2$

Y = CR', N, P

GERMOLE CONTAINING CONJUGATED MOLECULES AND POLYMERS

CROSS-REFERENCE TO RELATED APPLICATIONS

This application is the U.S. national stage application of International Patent Application No. PCT/US2012/026706, filed Feb. 27, 2012, which claims the benefit of U.S. Provisional Application Ser. No. 61/447,392, filed Feb. 28, 2011, the disclosures of which are hereby incorporated by reference in their entireties, including any figures, tables, or drawings.

The subject invention was made with government support under Contract No. FA950-09-1-0320 awarded by the Air Force Office of Scientific Research. The government has certain rights in the invention.

BACKGROUND OF INVENTION

Semiconducting polymers have been rapidly developed over the past decades. Solar cell and transistor devices have been designed that are based upon solution processable organic semiconducting polymers. Preparation of these devices is commercially attractive from the expectation that processing these semiconductors by printing methods is potentially much less expensive than the equivalent devices constructed from conventional inorganic materials. If material design is successful organic electronics would be an attractive alternative to the established technologies. The two major barriers to introduction of organic-based devices has been their relative performance and the stability of organic-based devices over time, which are inferior to devices based on inorganic semiconductor materials such as silicon. Improvements in performance metrics, such as power conversion efficiency in solar cells and charge mobility in transistors, could rapidly result in new and larger markets for any of these materials that have adequate stability at ambient conditions.

Poly(3-hexylthiophene) (P3HT) has been the most attractive organic material for transistor and photovoltaic based devices since 2006, and has been extensively developed. However, P3HT has a maximum field-effect charge mobility of around 0.1 $cm^2V^{-1}s^{-1}$. An approach taken toward increasing the charge carrier mobility in organic polymers has focused on fused aromatic rings to assure planarity of the aromatic units, which effectively extends the conjugation length and allows greater delocalization of injected charge carriers along a polymer backbone. In addition to the increase of conjugation length, fusion of rings promotes pi-pi stacking and other favorable intermolecular interactions between the large area coplanar aromatic segments of adjacent polymer chains to allow relatively efficient electrical transfer between chains. However, homopolymers of fused heterocycles often tend to be unstable, and the HOMO-LUMO levels of these homopolymers are generally not aligned with those of the fullerenes, limiting their use in bulk heterojunction solar cells The stability shortcomings of fused ring homopolymers have been overcome by copolymerization. For example cyclopentadithiophene (CPDT), shown below, has been incorporated in copolymers that achieve charge mobilities of more than 1 $cm^2V^{-1}s^{-1}$ in a transistor, and greater than 5% power conversion efficiency (PCE) in solar cells. Copolymers based on dithienosilole (DTS), shown below, display charge carrier mobilities approaching 1 $cm^2V^{-1}s^{-1}$, and have displayed PCE's that exceed 6%.

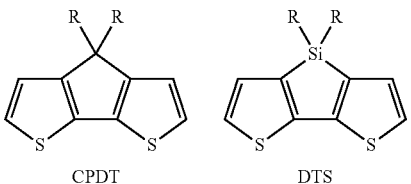

A donor-acceptor D-A approach to copolymers has allowed the tuning of frontier orbital energy levels of copolymers, allowing the modification of absorption by these materials. Tuning of the ultraviolet, visible, and near-infrared absorption bands of conjugated copolymers has been achieved by the alternation of electron-rich (donor, D) and electron-poor (acceptor, A) segments. The D-A copolymer approach has been used to tune the copolymer structure to achieve favorable optical and electronic properties for application such as field-effect transistors, light emitting diodes, and photovoltaics. An additional advantage of using the D-A copolymer approach has been greater stability to ambient atmosphere conditions due to a decrease in the energy level of both occupied and unoccupied molecular orbitals.

As indicated above, the inclusion of the silicon atom for a carbon atom in the fused ring unit allows relatively high charge carrier mobilities, which has been attributed to the interaction of the σ* orbital of the Si with the π* orbitals of the conjugated carbon system and to the changes in steric considerations due to the increased bond length of C—Si bonds over C—C bonds in otherwise equivalent polymers. This difference does not only change the structure of the individual copolymer chains, but also effects the interaction of adjacent chains, for example the ability to stack the flat aromatic groups of nearest neighbor chains, allowing closer, better aligned interactions are facilitated on the intermolecular level. To this end, improvements by the inclusion of Ge for C or Si is of interest; however, there are few examples of fused ring Ge molecules or polymers containing these molecules.

BRIEF SUMMARY

Embodiments of the invention are directed to Ge comprising heterocyclic compounds, homopolymers, thereof and copolymers thereof. The Ge comprising heterocyclic compounds can be selected from:

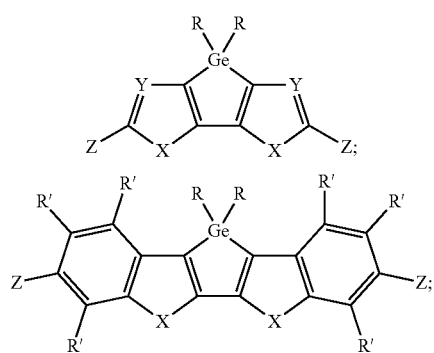

-continued

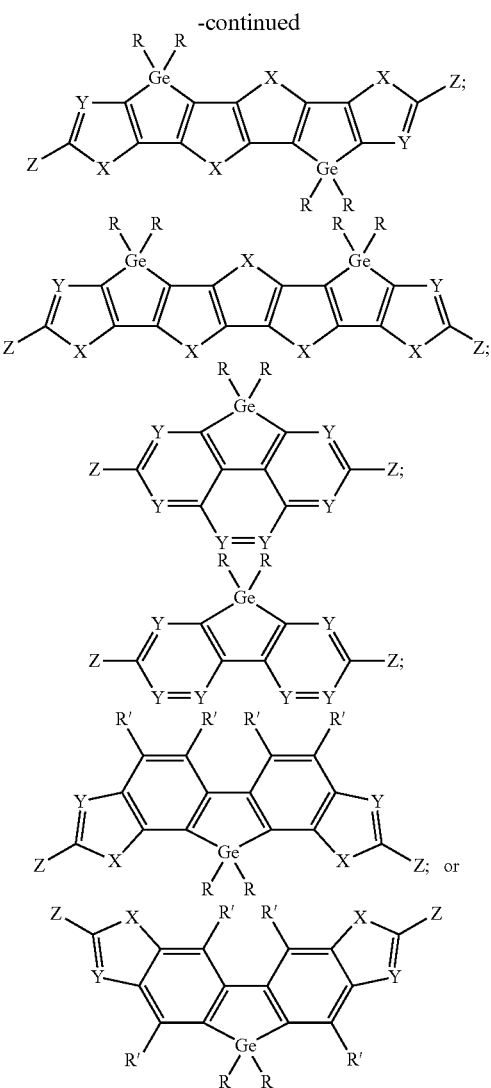

where: X is independently CR'$_2$, SiR'$_2$, NR', PR', P(O)R', O, S, SO, SO$_2$ Se, SeO, SeO$_2$, Te, TeO, or TeO$_2$; Y is CR', N, or P, and where at least one of X and Y is not CR'$_2$ or CR'; R is independently substituted or unsubstituted $C_1$-$C_{30}$ alkyl, $C_2$-$C_{30}$ alkenyl, $C_2$-$C_{30}$ alkynyl, $C_6$-$C_{14}$ aryl, $C_7$-$C_{30}$ arylalkyl, $C_8$-$C_{30}$ arylalkenyl, or $C_8$-$C_{30}$ arylalkynyl where one or more substituents, R', can be at any carbon of the R group; R' is independently H, $C_1$-$C_{30}$ alkyl, $C_2$-$C_{30}$ alkenyl, $C_2$-$C_{30}$ alkynyl, $C_6$-$C_{14}$ aryl, $C_7$-$C_{30}$ arylalkyl, $C_8$-$C_{30}$ arylalkenyl, $C_8$-$C_{30}$ arylalkynyl, hydroxy, $C_1$-$C_{30}$ alkoxy, $C_6$-$C_{14}$ aryloxy, $C_7$-$C_{30}$ arylalkyloxy, $C_2$-$C_{30}$ alkenyloxy, $C_2$-$C_{30}$ alkynyloxy, $C_8$-$C_{30}$ arylalkenyloxy, $C_8$-$C_{30}$ arylalkynyloxy, CO$_2$H, $C_2$-$C_{30}$ alkylester, $C_7$-$C_{15}$ arylester, $C_8$-$C_{30}$ alkylarylester, $C_3$-$C_{30}$ alkenylester, $C_3$-$C_{30}$ alkynylester, NH$_2$, $C_1$-$C_{30}$ alkylamino, $C_6$-$C_{14}$ arylamino, $C_7$-$C_{30}$ (arylalkyl)amino, $C_2$-$C_{30}$ alkenylamino, $C_2$-$C_{30}$ alkynylamino, $C_8$-$C_{30}$ (arylalkenyl)amino, $C_8$-$C_{30}$ (arylalkynyl)amino, $C_2$-$C_{30}$ dialkylamino, $C_{12}$-$C_{28}$ diarylamino, $C_4$-$C_{30}$ dialkenylamino, $C_4$-$C_{30}$ dialkynylamino, $C_7$-$C_{30}$ aryl(alkyl)amino, $C_7$-$C_{30}$ di(arylalkyl)amino, $C_8$-$C_{30}$ alkyl(arylalkyl)amino, $C_{15}$-$C_{30}$ aryl(arylalkyl)amino, $C_8$-$C_{30}$ alkenyl(aryl)amino, $C_8$-$C_{30}$ alkynyl(aryl) amino C(O)NH$_2$ (amido), $C_2$-$C_{30}$ alkylamido, $C_7$-$C_{14}$ arylamido, $C_8$-$C_{30}$ (arylalkyl)amido, $C_2$-$C_{30}$ dialkylamido, $C_{12}$-$C_{28}$ diarylamido, $C_8$-$C_{30}$ aryl(alkyl)amido, $C_{15}$-$C_{30}$ di(a- rylalkyl)amido, $C_9$-$C_{30}$ alkyl(arylalkyl)amido, $C_{16}$-$C_{30}$ aryl (arylalkyl)amido, thiol, $C_1$-$C_{30}$ alkyhydroxy, $C_6$-$C_{14}$ arylhydroxy, $C_7$-$C_{30}$ arylalkylhydroxy, $C_3$-$C_{30}$ alkenylhydroxy, $C_3$-$C_{30}$ alkynylhydroxy, $C_8$-$C_{30}$ arylalkenylhydroxy, $C_8$-$C_{30}$ arylalkynylhydroxy, $C_3$-$C_{30}$ polyether, $C_3$-$C_{30}$ polyether-ester, $C_3$-$C_{30}$ polyester, $C_3$-$C_{30}$ polyamino, $C_3$-$C_{30}$ polyaminoamido, $C_3$-$C_{30}$ polyaminoether, $C_3$-$C_{30}$ polyaminoester, or $C_3$-$C_{30}$ polyamidoester; and Z is H, Cl, Br, I, triflate, B(OH)$_2$, 4,4,5,5-tetramethylborolan-2-yl, 5,5-dimethylborinan-2-yl, R"$_3$Sn where R" is $C_1$-$C_6$ alkyl, MgCl, MgBr, MgI, (R"O)$_3$Si where R" is $C_1$-$C_2$ alkyl, R"$_3$Si where R" is independently methyl or benzyl, Me$_{3-x}$F$_x$Si, ZnCl, ZnBr, or ZnI.

According to embodiments of the invention, a polymer comprises a plurality of Ge comprising heterocyclic units derived from one or more of the Ge comprising heterocyclic compounds, where the compound absent the Z units is a repeating unit of the polymer. In one embodiment of the invention the polymer is a homopolymer having a plurality of like Ge comprising heterocyclic units. In an embodiment of the invention, the polymer is a copolymer having a plurality of at least two different Ge comprising heterocyclic units. In an embodiment of the invention a copolymer has a plurality of at least one of the Ge comprising heterocyclic units and at least one other conjugated repeating unit. In an embodiment of the invention, the other conjugated unit comprises an acceptor unit, such as thieno[3,4-c]pyrrolo-4,6-dione, benzo[c][1,2,5] thiadiazole, benzo[c][1,2,5]oxadiazole, benzo[d][1,2,3]triazole, pyrido[3,4-b]pyrazine, cyanovinylene, thiazolo[5,4-d] thiazole, 1,3,4-thiadiazole, pyrrolo[3,4-c]pyrrole-1,4-dione, 2,2'-bithiazole, [1,2,5]thiadiazolo[3,4-c]pyridine, thieno[3,4-b]pyrazine, [1,2,5]oxadiazolo[3,4-c]pyridine, dicyanovinylene, benzo[1,2-c;4,5-c']bis[1,2,5]thiadiazole, [1,2,5]thiadiazolo[3,4-g]quinoxaline, quinoxaline, 4-dicyanomethylenecyclopentadithiolene, benzo[c] thiophene or any derivative thereof. Embodiments of the invention are directed to a method of preparing a polymer comprising a plurality of Ge comprising heterocyclic units by a condensation method including Suzuki coupling, Stille coupling, Kumada coupling, Hiyama coupling, or Negishi coupling.

Other embodiments of the invention are directed to electrical devices that comprise the Ge comprising heterocyclic compound or the polymer having the Ge comprising heterocyclic repeating units. The device can be a bulk heterojunction solar cell, bilayer solar cell, multilayer solar cell, field effect transistor, diode, photodiode, light emitting device (LED), photovoltaic device, anti-stat conductor, transparent conductor, supercapacitor, battery, dye sensitized solar cell, electronic paper, electrochromic window, electrochromic display, or electrochromic mirror.

DETAILED DISCLOSURE

Figure 1:
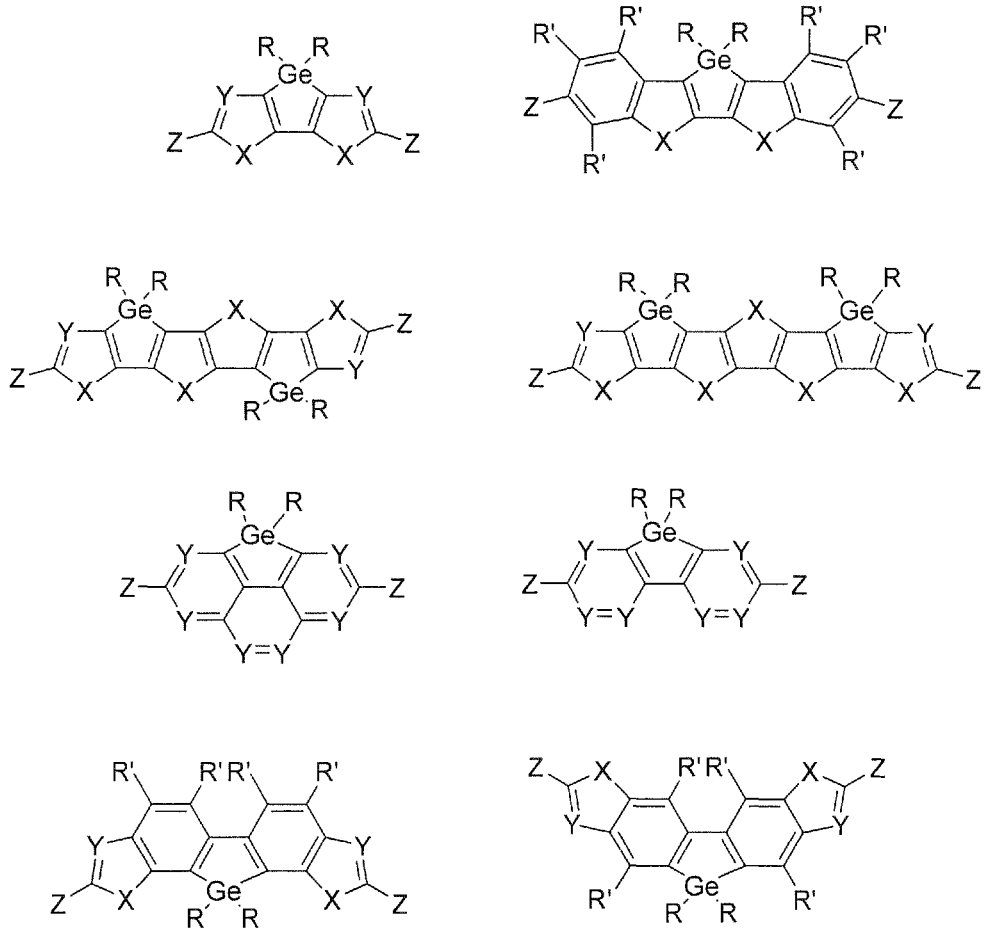
FIG. 1 shows the structure of Ge comprising fused ring heterocyclic compounds according to embodiments of the invention.

Embodiments of the invention are directed to Ge comprising fused ring heterocycle comprising compounds, such as dithienogermole (DTG), shown in FIG. 1, and the incorporation of the Ge comprising fused ring heterocycle units from these compounds into polymers and copolymers. These polymers and copolymers can be used as active semiconductor and light absorbing or emitting layers according to embodiments of the invention. The novel germoles have a germanium atom bridging two aromatic heterocyclic rings, for example, thiophene rings. In embodiments of the invention, the Ge comprising fused ring heterocycles are functionalized with a plurality of reactive substituents on a plurality of the rings; for example, bis- or even tris-, or tetrakis-tin, boron, or halide comprising monomers are possible, for example, a bis-substituted DTG with substituents at the 5 and 5' positions of the two thiophene rings. Another embodiment of the invention is directed to polymerization or copolymerization of Ge comprising fused ring heterocycles monomers with a self- or cross-complementary conjugated monomer. In an embodiment of the invention, the Ge containing fused ring heterocycle repeating units comprise a donor unit that can be polymerized with a conjugated monomer that is an acceptor unit to achieve a polymer with alternating D and A units such that the properties of the resulting donor-acceptor (DA) copolymer can be tuned by the copolymer composition. Polymers and copolymers containing Ge comprising fused ring heterocycles monomers, according to embodiments of the invention, are intrinsically conductive plastics that can be used in devices including: bulk heterojunction solar cells; bilayer or multilayer solar cells; field effect transistors; diodes and photodiodes; light emitting devices; photovoltaic devices; antistatic conductors and transparent conductors; supercapacitors, batteries, and other energy storage devices; dye sensitized solar cells; electronic paper; and electrochromic windows, displays, and mirrors.

In an embodiment of the invention the Ge comprising fused ring heterocycle units can have the structure:

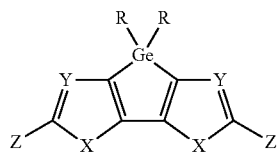

where: X is independently $CR'_2$, $SiR'_2$, N—R', PR', P(O)R', O, S, SO, $SO_2$ Se, SeO, $SeO_2$, Te, TeO, or $TeO_2$; Y is CR', N, or P, and where at least one of X and Y is not $CR'_2$ or CR'; R is independently substituted or unsubstituted $C_1$-$C_{30}$ alkyl, $C_2$-$C_{30}$ alkenyl, $C_2$-$C_{30}$ alkynyl, $C_6$-$C_{14}$ aryl, $C_7$-$C_{30}$ arylalkyl, $C_8$-$C_{30}$ arylalkenyl, or $C_8$-$C_{30}$ arylalkynyl, $C_1$-$C_{30}$ alkoxy, $C_6$-$C_{14}$ aryloxy, $C_7$-$C_{30}$ arylalkyloxy, $C_2$-$C_{30}$ alkenyloxy, $C_2$-$C_{30}$ alkynyloxy, $C_8$-$C_{30}$ arylalkenyloxy, $C_8$-$C_{30}$ arylalkynyloxy, $C_1$-$C_{30}$ alkylamino, $C_6$-$C_{14}$ arylamino, $C_7$-$C_{30}$ (arylalkyl)amino, $C_2$-$C_{30}$ alkenylamino, $C_2$-$C_{30}$ alkynylamino, $C_8$-$C_{30}$ (arylalkenyl)amino, $C_8$-$C_{30}$ (arylalkynyl)amino, $C_2$-$C_{30}$ dialkylamino, $C_{12}$-$C_{28}$ diarylamino, $C_4$-$C_{30}$ dialkenylamino, $C_4$-$C_{30}$ dialkynylamino, $C_7$-$C_{30}$ aryl(alkyl)amino, $C_7$-$C_{30}$ di(arylalkyl)amino, $C_8$-$C_{30}$ alkyl(arylalkyl)amino, $C_{15}$-$C_{30}$ aryl(arylalkyl)amino, $C_8$-$C_{30}$ alkenyl(aryl)amino, $C_8$-$C_{30}$ alkynyl(aryl)amino, $C_1$-$C_{30}$ alkylthio, $C_6$-$C_{14}$ arylthio, $C_7$-$C_{30}$ arylalkylthio, $C_2$-$C_{30}$ alkenylthio, $C_2$-$C_{30}$ alkynylthio, $C_8$-$C_{30}$ arylalkenylthio, or $C_8$-$C_{30}$ arylalkynylthio, where one or more substituents, R', can be at any carbon of the R group; R' is independently H, $C_1$-$C_{30}$ alkyl, $C_2$-$C_{30}$ alkenyl, $C_2$-$C_{30}$ alkynyl, $C_6$-$C_{14}$ aryl, $C_7$-$C_{30}$ arylalkyl, $C_8$-$C_{30}$ arylalkenyl, $C_8$-$C_{30}$ arylalkynyl, hydroxy, $C_1$-$C_{30}$ alkoxy, $C_6$-$C_{14}$ aryloxy, $C_7$-$C_{30}$ arylalkyloxy, $C_2$-$C_{30}$ alkenyloxy, $C_2$-$C_{30}$ alkynyloxy, $C_8$-$C_{30}$ arylalkenyloxy, $C_8$-$C_{30}$ arylalkynyloxy, $CO_2H$ or salt thereof, $C_2$-$C_{30}$ alkylester, $C_7$-$C_{15}$ arylester, $C_8$-$C_{30}$ alkylarylester, $C_3$-$C_{30}$ alkenylester, $C_3$-$C_{30}$ alkynylester, $NH_2$ or salt thereof, $C_1$-$C_{30}$ alkylamino or salt thereof, $C_6$-$C_{14}$ arylamino or salt thereof, $C_7$-$C_{30}$ (arylalkyl)amino or salt thereof, $C_2$-$C_{30}$ alkenylamino or salt thereof, $C_2$-$C_{30}$ alkynylamino or salt thereof, $C_8$-$C_{30}$ (arylalkenyl)amino or salt thereof, $C_8$-$C_{30}$ (arylalkynyl) amino or salt thereof, $C_2$-$C_{30}$ dialkylamino or salt thereof, $C_{12}$-$C_{28}$ diarylamino or salt thereof, $C_4$-$C_{30}$ dialkenylamino or salt thereof, $C_4$-$C_{30}$ dialkynylamino or salt thereof, $C_7$-$C_{30}$ aryl(alkyl)amino or salt thereof, $C_7$-$C_{30}$ di(arylalkyl)amino or salt thereof, $C_8$-$C_{30}$ alkyl(arylalkyl)amino or salt thereof, $C_{15}$-$C_{30}$ aryl(arylalkyl)amino or salt thereof, $C_8$-$C_{30}$ alkenyl(aryl)amino or salt thereof, $C_8$-$C_{30}$ alkynyl(aryl)amino or salt thereof, $C(O)NH_2$ (amido), $C_2$-$C_{30}$ alkylamido, $C_7$-$C_{14}$ arylamido, $C_8$-$C_{30}$ (arylalkyl)amido, $C_2$-$C_{30}$ dialkylamido, $C_{12}$-$C_{28}$ diarylamido, $C_8$-$C_{30}$ aryl(alkyl)amido, $C_{15}$-$C_{30}$ di(arylalkyl)amido, $C_9$-$C_{30}$ alkyl(arylalkyl)amido, $C_{16}$-$C_{30}$ aryl(arylalkyl)amido, thiol, $C_1$-$C_{30}$ alkylhydroxy, $C_6$-$C_{14}$ arylhydroxy, $C_7$-$C_{30}$ arylalkylhydroxy, $C_3$-$C_{30}$ alkenylhydroxy, $C_3$-$C_{30}$ alkynylhydroxy, $C_8$-$C_{30}$ arylalkenylhydroxy, $C_8$-$C_{30}$ arylalkynylhydroxy, $C_3$-$C_{30}$ polyether, $C_3$-$C_{30}$ polyetherester, $C_3$-$C_{30}$ polyester, $C_3$-$C_{30}$ polyamino, $C_3$-$C_{30}$ polyaminoamido, $C_3$-$C_{30}$ polyaminoether, $C_3$-$C_{30}$ polyaminoester, $C_3$-$C_{30}$ polyamidoester, $C_1$-$C_{30}$ alkylthio, $C_6$-$C_{14}$ arylthio, $C_7$-$C_{30}$ arylalkylthio, $C_2$-$C_{30}$ alkenylthio, $C_2$-$C_{30}$ alkynylthio, $C_8$-$C_{30}$ arylalkenylthio, $C_8$-$C_{30}$ arylalkynylthio, $S(O)_2OH$ or salt thereof, or $OP(O)(OH)_2$ or salt thereof; and Z is H, Cl, Br, I, triflate or other pseudohalogen, $B(OH)_2$, $B(OR'')_2$ where R'' is $C_1$-$C_6$ alkyl, 4,4,5,5-tetramethylborolan-2-yl, 5,5-dimethylborinan-2-yl, $R''_3Sn$ where R'' is $C_1$-$C_6$ alkyl, MgCl, MgBr, MgI, $(R''O)_3Si$ where R'' is $C_1$-$C_2$ alkyl, $R''_3Si$ where R'' is independently methyl or benzyl, $R''_{3-x}(R''O)_xSi$ where R'' are independently $C_1$-$C_6$ alkyl, $Me_{3-x}F_xSi$ where x is 1 to 3, ZnCl, ZnBr, ZnI, or any other reactive functionality that can be used for a condensation or addition polymerization or copolymerization to a conjugated polymer, where the C—Z bond is broken and a C—C bond is formed between a Ge comprising fused ring heterocycle unit and a second Ge comprising fused ring heterocycle unit or another conjugated unit. For example, the Z group can be one that is a functionality that is used in: Suzuki coupling; Stille coupling; Kumada coupling; Hiyama coupling; Negishi coupling; Yamamoto nickel mediated homocoupling; oxidative polymerization where oxidants include Fe (III) compounds, $NO^+$ salts, and other agents with reduction potentials greater than the oxidation potential of the DTG containing monomer; or any other polymerization method. In embodiments of the invention, the Z group is a portion of a polymeric chain bonded to the Ge comprising fused ring heterocycle repeating unit, where that portion can be as little as an end capping atom, for example a H atom, or as much as all other repeating units of a homopolymer or copolymer. In an embodiment of the invention the Ge comprising fused ring heterocycle units can have the structure:

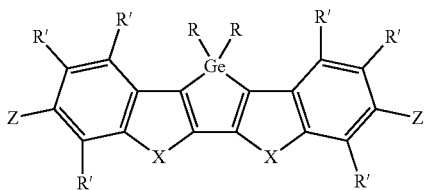

where: X is independently CR'$_2$, SiR'$_2$, N—R', PR', P(O)R', O, S, SO, SO$_2$ Se, SeO, SeO$_2$, Te, TeO, or TeO$_2$; and where at least one X is not CR'$_2$; R is independently substituted or unsubstituted C$_1$-C$_{30}$ alkyl, C$_2$-C$_{30}$ alkenyl, C$_2$-C$_{30}$ alkynyl, C$_6$-C$_{14}$ aryl, C$_7$-C$_{30}$ arylalkyl, C$_8$-C$_{30}$ arylalkenyl, C$_8$-C$_{30}$ arylalkynyl, C$_1$-C$_{30}$ alkoxy, C$_6$-C$_{14}$ aryloxy, C$_7$-C$_{30}$ arylalkyloxy, C$_2$-C$_{30}$ alkenyloxy, C$_2$-C$_{30}$ alkynyloxy, C$_8$-C$_{30}$ arylalkenyloxy, C$_8$-C$_{30}$ arylalkynyloxy, C$_1$-C$_{30}$ alkylamino, C$_6$-C$_{14}$ arylamino, C$_7$-C$_{30}$ (arylalkyl)amino, C$_2$-C$_{30}$ alkenylamino, C$_2$-C$_{30}$ alkynylamino, C$_8$-C$_{30}$ (arylalkenyl)amino, C$_8$-C$_{30}$ (arylalkynyl)amino, C$_2$-C$_{30}$ dialkylamino, C$_{12}$-C$_{28}$ diarylamino, C$_4$-C$_{30}$ dialkenylamino, C$_4$-C$_{30}$ dialkynylamino, C$_7$-C$_{30}$ aryl(alkyl)amino, C$_7$-C$_{30}$ di(arylalkyl)amino, C$_8$-C$_{30}$ alkyl(arylalkyl)amino, C$_{15}$-C$_{30}$ aryl(arylalkyl)amino, C$_8$-C$_{30}$ alkenyl(aryl)amino, C$_8$-C$_{30}$ alkynyl(aryl)amino, C$_1$-C$_{30}$ alkylthio, C$_6$-C$_{14}$ arylthio, C$_7$-C$_{30}$ arylalkylthio, C$_2$-C$_{30}$ alkenylthio, C$_2$-C$_{30}$ alkynylthio, C$_8$-C$_{30}$ arylalkenylthio, or C$_8$-C$_3$ arylalkynylthio, where one or more substituents, R', can be at any carbon of the R group; R' is independently H, C$_1$-C$_{30}$ alkyl, C$_2$-C$_{30}$ alkenyl, C$_2$-C$_{30}$ alkynyl, C$_6$-C$_{14}$ aryl, C$_7$-C$_{30}$ arylalkyl, C$_8$-C$_{30}$ arylalkenyl, C$_8$-C$_{30}$ arylalkynyl, hydroxy, C$_1$-C$_{30}$ alkoxy, C$_6$-C$_{14}$ aryloxy, C$_7$-C$_{30}$ arylalkyloxy, C$_2$-C$_{30}$ alkenyloxy, C$_2$-C$_{30}$ alkynyloxy, C$_8$-C$_{30}$ arylalkenyloxy, C$_8$-C$_{30}$ arylalkynyloxy, CO$_2$H or salt thereof, C$_2$-C$_{30}$ alkylester, C$_7$-C$_{15}$ arylester, C$_8$-C$_{30}$ alkylarylester, C$_3$-C$_{30}$ alkenylester, C$_3$-C$_{30}$ alkynylester, NH$_2$ or salt thereof, C$_1$-C$_{30}$ alkylamino or salt thereof, C$_6$-C$_{14}$ arylamino or salt thereof, C$_7$-C$_{30}$ (arylalkyl)amino or salt thereof, C$_2$-C$_{30}$ alkenylamino or salt thereof, C$_2$-C$_{30}$ alkynylamino or salt thereof, C$_8$-C$_{30}$ (arylalkenyl)amino or salt thereof, C$_8$-C$_{30}$ (arylalkynyl)amino or salt thereof, C$_2$-C$_{30}$ dialkylamino or salt thereof, C$_{12}$-C$_{28}$ diarylamino or salt thereof, C$_4$-C$_{30}$ dialkenylamino or salt thereof, C$_4$-C$_{30}$ dialkynylamino or salt thereof, C$_7$-C$_{30}$ aryl(alkyl)amino or salt thereof, C$_7$-C$_{30}$ di(arylalkyl)amino or salt thereof, C$_8$-C$_{30}$ alkyl(arylalkyl)amino or salt thereof, C$_{15}$-C$_{30}$ aryl(arylalkyl)amino or salt thereof, C$_8$-C$_{30}$ alkenyl(aryl)amino or salt thereof, C$_8$-C$_{30}$ alkynyl(aryl)amino or salt thereof, C(O)NH$_2$ (amido), C$_2$-C$_{30}$ alkylamido, C$_7$-C$_{14}$ arylamido, C$_8$-C$_{30}$ (arylalkyl)amido, C$_2$-C$_{30}$ dialkylamido, C$_{12}$-C$_{28}$ diarylamido, C$_8$-C$_{30}$ aryl(alkyl)amido, C$_{15}$-C$_{30}$ di(arylalkyl)amido, C$_9$-C$_{30}$ alkyl(arylalkyl)amido, C$_{16}$-C$_{30}$ aryl(arylalkyl)amido, thiol, C$_1$-C$_{30}$ alkyhydroxy, C$_6$-C$_{14}$ arylhydroxy, C$_7$-C$_{30}$ arylalkylhydroxy, C$_3$-C$_{30}$ alkenylhydroxy, C$_3$-C$_{30}$ alkynylhydroxy, C$_8$-C$_{30}$ arylalkenylhydroxy, C$_8$-C$_{30}$ arylalkynylhydroxy, C$_3$-C$_{30}$ polyether, C$_3$-C$_{30}$ polyetherester, C$_3$-C$_{30}$ polyester C$_3$-C$_{30}$ polyamino, C$_3$-C$_{30}$ polyaminoamido, C$_3$-C$_{30}$ polyaminoether, C$_3$-C$_{30}$ polyaminoester, C$_3$-C$_{30}$ polyamidoester, C$_1$-C$_{30}$ alkylthio, C$_6$-C$_{14}$ arylthio, C$_7$-C$_{30}$ arylalkylthio, C$_2$-C$_{30}$ alkenylthio, C$_2$-C$_{30}$ alkynylthio, C$_8$-C$_{30}$ arylalkenylthio, C$_8$-C$_{30}$ arylalkynylthio, S(O)$_2$OH or salt thereof, or OP(O)(OH)$_2$ or salt thereof; and Z is H, Cl, Br, I, triflate or other pseudohalogen, B(OH)$_2$, B(OR")$_2$ where R" is C$_1$-C$_6$ alkyl, 4,4,5,5-tetramethylborolan-2-yl, 5,5-dimethylborinan-2-yl, R"$_3$Sn where R" is C$_1$-C$_6$ alkyl, MgCl, MgBr, MgI, (R"O)$_3$Si where R" is C$_1$-C$_2$ alkyl, R"$_3$Si where R" is independently methyl or benzyl, R"$_{3-x}$(R"O)$_x$Si where R" are independently C$_1$-C$_6$ alkyl, Me$_{3-x}$F$_x$Si where x is 1 to 3, ZnCl, ZnBr, ZnI, or any other reactive functionality that can be used for a condensation or addition polymerization or copolymerization to a conjugated polymer, where the C—Z bond is broken and a C—C bond is formed between a Ge comprising fused ring heterocycle unit and a second Ge comprising fused ring heterocycle unit or another conjugated unit. For example, the Z group can be one that is a functionality that is used in: Suzuki coupling; Stille coupling; Kumada coupling; Hiyama coupling; Negishi coupling; Yammamoto nickel mediated homocoupling; oxidative polymerization where oxidants include Fe (III) compounds, NO$^+$ salts, and other agents with reduction potentials greater than the oxidation potential of the DTG containing monomer; or any other polymerization method. In embodiments of the invention, the Z group is a portion of a polymeric chain bonded to the Ge comprising fused ring heterocycle repeating unit, where that portion can be as little as an end capping atom, for example, a H atom, or as much as all other repeating units of a homopolymer or copolymer.

In an embodiment of the invention the Ge comprising fused ring heterocycle units can have the structure:

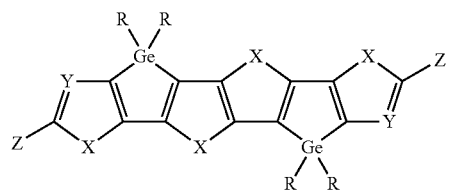

where: X is independently CR'$_2$, SiR'$_2$, N—R', PR', P(O)R', O, S, SO, SO$_2$ Se, SeO, SeO$_2$, Te, TeO, or TeO$_2$; Y is CR', N, or P, and where at least one of X and Y is not CR'$_2$ or CR'; R is independently substituted or unsubstituted C$_1$-C$_{30}$ alkyl, C$_2$-C$_{30}$ alkenyl, C$_2$-C$_{30}$ alkynyl, C$_6$-C$_{14}$ aryl, C$_7$-C$_{30}$ arylalkyl, C$_8$-C$_{30}$ arylalkenyl, C$_8$-C$_{30}$ arylalkynyl, C$_1$-C$_{30}$ alkoxy, C$_6$-C$_{14}$ aryloxy, C$_7$-C$_{30}$ arylalkyloxy, C$_2$-C$_{30}$ alkenyloxy, C$_2$-C$_{30}$ alkynyloxy, C$_8$-C$_{30}$ arylalkenyloxy, C$_8$-C$_{30}$ arylalkynyloxy, C$_1$-C$_{30}$ alkylamino, C$_6$-C$_{14}$ arylamino, C$_7$-C$_{30}$ (arylalkyl)amino, C$_2$-C$_{30}$ alkenylamino, C$_2$-C$_{30}$ alkynylamino, C$_8$-C$_{30}$ (arylalkenyl)amino, C$_8$-C$_{30}$ (arylalkynyl)amino, C$_2$-C$_{30}$ dialkylamino, C$_{12}$-C$_{28}$ diarylamino, C$_4$-C$_{30}$ dialkenylamino, C$_4$-C$_{30}$ dialkynylamino, C$_7$-C$_{30}$ aryl(alkyl)amino, C$_7$-C$_{30}$ di(arylalkyl)amino, C$_8$-C$_{30}$ alkyl(arylalkyl)amino, C$_{15}$-C$_{30}$ aryl(arylalkyl)amino, C$_8$-C$_{30}$ alkenyl(aryl)amino, C$_8$-C$_{30}$ alkynyl(aryl)amino, C$_1$-C$_{30}$ alkylthio, C$_6$-C$_{14}$ arylthio, C$_7$-C$_{30}$ arylalkylthio, C$_2$-C$_{30}$ alkenylthio, C$_2$-C$_{30}$ alkynylthio, C$_8$-C$_{30}$ arylalkenylthio, or C$_8$-C$_{30}$ arylalkynylthio, where one or more substituents, R', can be at any carbon of the R group; R' is independently H, C$_1$-C$_{30}$ alkyl, C$_2$-C$_{30}$ alkenyl, C$_2$-C$_{30}$ alkynyl, C$_6$-C$_{14}$ aryl, C$_7$-C$_{30}$ arylalkyl, C$_8$-C$_{30}$ arylalkenyl, C$_8$-C$_{30}$ arylalkynyl, hydroxy, C$_1$-C$_{30}$ alkoxy, C$_6$-C$_{14}$ aryloxy, C$_7$-C$_{30}$ arylalkyloxy, C$_2$-C$_{30}$ alkenyloxy, C$_2$-C$_{30}$ alkynyloxy, C$_8$-C$_{30}$ arylalkenyloxy, C$_8$-C$_{30}$ arylalkynyloxy, CO$_2$H or salt thereof, C$_2$-C$_{30}$ alkylester, C$_7$-C$_{15}$ arylester, C$_8$-C$_{30}$ alkylarylester, C$_3$-C$_{30}$ alkenylester, C$_3$-C$_{30}$ alkynylester, NH$_2$ or salt thereof, C$_1$-C$_{30}$ alkylamino or salt thereof, C$_6$-C$_{14}$ arylamino or salt thereof, C$_7$-C$_{30}$ (arylalkyl)amino or salt thereof, C$_2$-C$_{30}$ alkenylamino or salt thereof, C$_2$-C$_{30}$ alkynylamino or salt thereof, C$_8$-C$_{30}$ (arylalkenyl)amino or salt thereof, C$_8$-C$_{30}$ (arylalkynyl)amino or salt thereof, C$_2$-C$_{30}$ dialkylamino or salt thereof, C$_{12}$-C$_{28}$ diarylamino or salt thereof, C$_4$-C$_{30}$ dialkenylamino or salt thereof, C$_4$-C$_{30}$ dialkynylamino or salt thereof, C$_7$-C$_{30}$ aryl(alkyl)amino or salt thereof, C$_7$-C$_{30}$ di(arylalkyl)amino or salt thereof, $C_8$-$C_{30}$ alkyl(arylalkyl)amino or salt thereof, $C_{15}$-$C_{30}$ aryl(arylalkyl)amino or salt thereof, $C_8$-$C_{30}$ alkenyl(aryl)amino or salt thereof, $C_8$-$C_{30}$ alkynyl(aryl)amino or salt thereof, C(O)NH$_2$ (amido), $C_2$-$C_{30}$ alkylamido, $C_7$-$C_{14}$ arylamido, $C_8$-$C_{30}$ (arylalkyl)amido, $C_2$-$C_{30}$ dialkylamido, $C_{12}$-$C_{28}$ diarylamido, $C_8$-$C_{30}$ aryl(alkyl)amido, $C_{15}$-$C_{30}$ di(arylalkyl)amido, $C_9$-$C_{30}$ alkyl(arylalkyl)amido, $C_{16}$-$C_{30}$ aryl(arylalkyl)amido, thiol, $C_1$-$C_{30}$ alkylhydroxy, $C_6$-$C_{14}$ arylhydroxy, $C_7$-$C_{30}$ arylalkylhydroxy, $C_3$-$C_{30}$ alkenylhydroxy, $C_3$-$C_{30}$ alkynylhydroxy, $C_8$-$C_{30}$ arylalkenylhydroxy, $C_8$-$C_{30}$ arylalkynylhydroxy, $C_3$-$C_{30}$ polyether, $C_3$-$C_{30}$ polyetherester, $C_3$-$C_{30}$ polyester $C_3$-$C_{30}$ polyamino, $C_3$-$C_{30}$ polyaminoamido, $C_3$-$C_{30}$ polyaminoether, $C_3$-$C_{30}$ polyaminoester, $C_3$-$C_{30}$ polyamidoester, $C_1$-$C_{30}$ alkylthio, $C_6$-$C_{14}$ arylthio, $C_7$-$C_{30}$ arylalkylthio, $C_2$-$C_{30}$ alkenylthio, $C_2$-$C_{30}$ alkynylthio, $C_8$-$C_{30}$ arylalkenylthio, $C_8$-$C_{30}$ arylalkynylthio, S(O)$_2$OH or salt thereof, or OP(O)(OH)$_2$ or salt thereof; and Z is H, Cl, Br, I, triflate or other pseudohalogen, B(OH)$_2$, B(OR")$_2$ where R" is $C_1$-$C_6$ alkyl, 4,4,5,5-tetramethylborolan-2-yl, 5,5-dimethylborinan-2-yl, R"$_3$Sn where R" is $C_1$-$C_6$ alkyl, MgCl, MgBr, MgI, (R"O)$_3$Si where R" is $C_1$-$C_2$ alkyl, R"$_3$Si where R" is independently methyl or benzyl, R"$_{3-x}$(R"O)$_x$Si where R" are independently $C_1$-$C_6$ alkyl, Me$_{3-x}$F$_x$Si where x is 1 to 3, ZnCl, ZnBr, ZnI, or any other reactive functionality that can be used for a condensation or addition polymerization or copolymerization to a conjugated polymer, where the C—Z bond is broken and a C—C bond is formed between a Ge comprising fused ring heterocycle unit and a second Ge comprising fused ring heterocycle unit or another conjugated unit. For example, the Z group can be one that is a functionality that is used in: Suzuki coupling; Stille coupling; Kumada coupling; Hiyama coupling; Negishi coupling; Yammamoto nickel mediated homocoupling; oxidative polymerization where oxidants include Fe (III) compounds, NO$^+$ salts, and other agents with reduction potentials greater than the oxidation potential of the DTG containing monomer; or any other polymerization method. In embodiments of the invention, the Z group is a portion of a polymeric chain bonded to the Ge comprising fused ring heterocycle repeating unit, where that portion can be as little as an end capping atom, for example a H atom, or as much as all other repeating units of a homopolymer or copolymer.

In an embodiment of the invention the Ge comprising fused ring heterocycle units can have the structure:

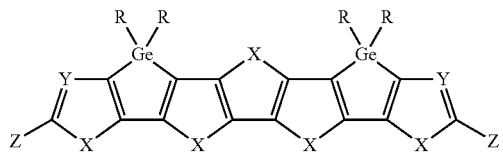

where: X is independently CR'$_2$, SiR'$_2$, N—R', PR', P(O)R', O, S, SO, SO$_2$ Se, SeO, SeO$_2$, Te, TeO, or TeO$_2$; Y is CR', N, or P, and where at least one of X and Y is not CR'$_2$ or CR'; R is independently substituted or unsubstituted $C_1$-$C_{30}$ alkyl, $C_2$-$C_{30}$ alkenyl, $C_2$-$C_{30}$ alkynyl, $C_6$-$C_{14}$ aryl, $C_7$-$C_{30}$ arylalkyl, $C_8$-$C_{30}$ arylalkenyl, $C_8$-$C_{30}$ arylalkynyl, $C_1$-$C_{30}$ alkoxy, $C_6$-$C_{14}$ aryloxy, $C_7$-$C_{30}$ arylalkyloxy, $C_2$-$C_{30}$ alkenyloxy, $C_2$-$C_{30}$ alkynyloxy, $C_8$-$C_{30}$ arylalkenyloxy, $C_8$-$C_{30}$ arylalkynyloxy, $C_1$-$C_{30}$ alkylamino, $C_6$-$C_{14}$ arylamino, $C_7$-$C_{30}$ (arylalkyl)amino, $C_2$-$C_{30}$ alkenylamino, $C_2$-$C_{30}$ alkynylamino, $C_8$-$C_{30}$ (arylalkenyl)amino, $C_8$-$C_{30}$ (arylalkynyl)amino, $C_2$-$C_{30}$ dialkylamino, $C_{12}$-$C_{28}$ diarylamino, $C_4$-$C_{30}$ dialkenylamino, $C_4$-$C_{30}$ dialkynylamino, $C_7$-$C_{30}$ aryl(alkyl)amino, $C_7$-$C_{30}$ di(arylalkyl)amino, $C_8$-$C_{30}$ alkyl(arylalkyl)amino, $C_{15}$-$C_{30}$ aryl(arylalkyl)amino, $C_8$-$C_{30}$ alkenyl(aryl)amino, $C_8$-$C_{30}$ alkynyl(aryl)amino, $C_1$-$C_{30}$ alkylthio, $C_6$-$C_{14}$ arylthio, $C_7$-$C_{30}$ arylalkylthio, $C_2$-$C_{30}$ alkenylthio, $C_2$-$C_{30}$ alkynylthio, $C_8$-$C_{30}$ arylalkenylthio, or $C_8$-$C_{30}$ arylalkynylthio, where one or more substituents, R', can be at any carbon of the R group; R' is independently H, $C_1$-$C_{30}$ alkyl, $C_2$-$C_{30}$ alkenyl, $C_2$-$C_{30}$ alkynyl, $C_6$-$C_{14}$ aryl, $C_7$-$C_{30}$ arylalkyl, $C_8$-$C_{30}$ arylalkenyl, $C_8$-$C_{30}$ arylalkynyl, hydroxy, $C_1$-$C_{30}$ alkoxy, $C_6$-$C_{14}$ aryloxy, $C_7$-$C_{30}$ arylalkyloxy, $C_2$-$C_{30}$ alkenyloxy, $C_2$-$C_{30}$ alkynyloxy, $C_8$-$C_{30}$ arylalkenyloxy, $C_8$-$C_{30}$ arylalkynyloxy, CO$_2$H or salt thereof, $C_2$-$C_{30}$ alkylester, $C_7$-$C_{15}$ arylester, $C_8$-$C_{30}$ alkylarylester, $C_3$-$C_{30}$ alkenylester, $C_3$-$C_{30}$ alkynylester, NH$_2$ or salt thereof, $C_1$-$C_{30}$ alkylamino or salt thereof, $C_6$-$C_{14}$ arylamino or salt thereof, $C_7$-$C_{30}$ (arylalkyl)amino or salt thereof, $C_2$-$C_{30}$ alkenylamino or salt thereof, $C_2$-$C_{30}$ alkynylamino or salt thereof, $C_8$-$C_{30}$ (arylalkenyl)amino or salt thereof, $C_8$-$C_{30}$ (arylalkynyl)amino or salt thereof, $C_2$-$C_{30}$ dialkylamino or salt thereof, $C_{12}$-$C_{28}$ diarylamino or salt thereof, $C_4$-$C_{30}$ dialkenylamino or salt thereof, $C_4$-$C_{30}$ dialkynylamino or salt thereof, $C_7$-$C_{30}$ aryl(alkyl)amino or salt thereof, $C_7$-$C_{30}$ di(arylalkyl)amino or salt thereof, $C_8$-$C_{30}$ alkyl(arylalkyl)amino or salt thereof, $C_{15}$-$C_{30}$ aryl(arylalkyl)amino or salt thereof, $C_8$-$C_{30}$ alkenyl(aryl)amino or salt thereof, $C_8$-$C_{30}$ alkynyl(aryl)amino or salt thereof, C(O)NH$_2$ (amido), $C_2$-$C_{30}$ alkylamido, $C_7$-$C_{14}$ arylamido, $C_8$-$C_{30}$ (arylalkyl)amido, $C_2$-$C_{30}$ dialkylamido, $C_{12}$-$C_{28}$ diarylamido, $C_8$-$C_{30}$ aryl(alkyl)amido, $C_{15}$-$C_{30}$ di(arylalkyl)amido, $C_9$-$C_{30}$ alkyl(arylalkyl)amido, $C_{16}$-$C_{30}$ aryl(arylalkyl)amido, thiol, $C_1$-$C_{30}$ alkylhydroxy, $C_6$-$C_{14}$ arylhydroxy, $C_7$-$C_{30}$ arylalkylhydroxy, $C_3$-$C_{30}$ alkenylhydroxy, $C_3$-$C_{30}$ alkynylhydroxy, $C_8$-$C_{30}$ arylalkenylhydroxy, $C_8$-$C_{30}$ arylalkynylhydroxy, $C_3$-$C_{30}$ polyether, $C_3$-$C_{30}$ polyetherester, $C_3$-$C_{30}$ polyester, $C_3$-$C_{30}$ polyamino, $C_3$-$C_{30}$ polyaminoamido, $C_3$-$C_{30}$ polyaminoether, $C_3$-$C_{30}$ polyaminoester, $C_3$-$C_{30}$ polyamidoester, $C_1$-$C_{30}$ alkylthio, $C_6$-$C_{14}$ arylthio, $C_7$-$C_{30}$ arylalkylthio, $C_2$-$C_{30}$ alkenylthio, $C_2$-$C_{30}$ alkynylthio, $C_8$-$C_{30}$ arylalkenylthio, $C_8$-$C_{30}$ arylalkynylthio, S(O)$_2$OH or salt thereof, or OP(O)(OH)$_2$ or salt thereof; and Z is H, Cl, Br, I, triflate or other pseudohalogen, B(OH)$_2$, B(OR")$_2$ where R" is $C_1$-$C_6$ alkyl, 4,4,5,5-tetramethylborolan-2-yl, 5,5-dimethylborinan-2-yl, R"$_3$Sn where R" is $C_1$-$C_6$ alkyl, MgCl, MgBr, MgI, (R"O)$_3$Si where R" is $C_1$-$C_2$ alkyl, R"$_3$Si where R" is independently methyl or benzyl, R"$_{3-x}$(R"O)$_x$Si where R" are independently $C_1$-$C_6$ alkyl, Me$_{3-x}$F$_x$Si where x is 1 to 3, ZnCl, ZnBr, ZnI, or any other reactive functionality that can be used for a condensation or addition polymerization or copolymerization to a conjugated polymer, where the C—Z bond is broken and a C—C bond is formed between a Ge comprising fused ring heterocycle unit and a second Ge comprising fused ring heterocycle unit or another conjugated unit. For example, the Z group can be one that is a functionality that is used in: Suzuki coupling; Stille coupling; Kumada coupling; Hiyama coupling; Negishi coupling; Yammamoto nickel mediated homocoupling; oxidative polymerization where oxidants include Fe (III) compounds, NO$^+$ salts, and other agents with reduction potentials greater than the oxidation potential of the DTG containing monomer; or any other polymerization method. In embodiments of the invention, the Z group is a portion of a polymeric chain bonded to the Ge comprising fused ring heterocycle repeating unit, where that portion can be as little as an end capping atom, for example a H atom, or as much as all other repeating units of a homopolymer or copolymer.

In an embodiment of the invention the Ge comprising fused ring heterocycle units can have the structure:

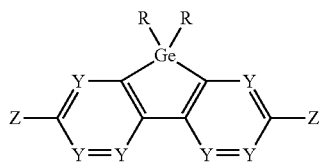

where: Y is CR', N, or P, and where at least one Y is not or CR'; and where at least one X is not CR'$_2$; R is independently substituted or unsubstituted $C_1$-$C_{30}$ alkyl, $C_2$-$C_{30}$ alkenyl, $C_2$-$C_{30}$ alkynyl, $C_6$-$C_{14}$ aryl, $C_7$-$C_{30}$ arylalkyl, $C_8$-$C_{30}$ arylalkenyl, $C_8$-$C_{30}$ arylalkynyl, $C_1$-$C_{30}$ alkoxy, $C_6$-$C_{14}$ aryloxy, $C_7$-$C_{30}$ arylalkyloxy, $C_2$-$C_{30}$ alkenyloxy, $C_2$-$C_{30}$ alkynyloxy, $C_8$-$C_{30}$ arylalkenyloxy, $C_8$-$C_{30}$ arylalkynyloxy, $C_1$-$C_{30}$ alkylamino, $C_6$-$C_{14}$ arylamino, $C_7$-$C_{30}$ (arylalkyl)amino, $C_2$-$C_{30}$ alkenylamino, $C_2$-$C_{30}$ alkynylamino, $C_8$-$C_{30}$ (arylalkenyl) amino, $C_8$-$C_{30}$ (arylalkynyl)amino, $C_2$-$C_{30}$ dialkylamino, $C_{12}$-$C_{28}$ diarylamino, $C_4$-$C_{30}$ dialkenylamino, $C_4$-$C_{30}$ dialkynylamino, $C_7$-$C_{30}$ aryl(alkyl)amino, $C_7$-$C_{30}$ di(arylalkyl) amino, $C_8$-$C_{30}$ alkyl(arylalkyl)amino, $C_{15}$-$C_{30}$ aryl(arylalkyl)amino, $C_8$-$C_{30}$ alkenyl(aryl)amino, $C_8$-$C_{30}$ alkynyl(aryl) amino, $C_1$-$C_{30}$ alkylthio, $C_6$-$C_{14}$ arylthio, $C_7$-$C_{30}$ arylalkylthio, $C_2$-$C_{30}$ alkenylthio, $C_2$-$C_{30}$ alkynylthio, $C_8$-$C_{30}$ arylalkenylthio, or $C_8$-$C_{30}$ arylalkynylthio, where one or more substituents, R', can be at any carbon of the R group; R' is independently H, $C_1$-$C_{30}$ alkyl, $C_2$-$C_{30}$ alkenyl, $C_2$-$C_{30}$ alkynyl, $C_6$-$C_{14}$ aryl, $C_7$-$C_{30}$ arylalkyl, $C_8$-$C_{30}$ arylalkenyl, $C_8$-$C_{30}$ arylalkynyl, hydroxy, $C_1$-$C_{30}$ alkoxy, $C_6$-$C_{14}$ aryloxy, $C_7$-$C_{30}$ arylalkyloxy, $C_2$-$C_{30}$ alkenyloxy, $C_2$-$C_{30}$ alkynyloxy, $C_8$-$C_{30}$ arylalkenyloxy, $C_8$-$C_{30}$ arylalkynyloxy, $CO_2H$ or salt thereof, $C_2$-$C_{30}$ alkylester, $C_7$-$C_{15}$ arylester, $C_8$-$C_{30}$ alkylarylester, $C_3$-$C_{30}$ alkenylester, $C_3$-$C_{30}$ alkynylester, $NH_2$ or salt thereof, $C_1$-$C_{30}$ alkylamino or salt thereof, $C_6$-$C_{14}$ arylamino or salt thereof, $C_7$-$C_{30}$ (arylalkyl)amino or salt thereof, $C_2$-$C_{30}$ alkenylamino or salt thereof, $C_2$-$C_{30}$ alkynylamino or salt thereof, $C_8$-$C_{30}$ (arylalkenyl)amino or salt thereof, $C_8$-$C_{30}$ (arylalkynyl)amino or salt thereof, $C_2$-$C_{30}$ dialkylamino or salt thereof, $C_{12}$-$C_{28}$ diarylamino or salt thereof, $C_4$-$C_{30}$ dialkenylamino or salt thereof, $C_4$-$C_{30}$ dialkynylamino or salt thereof, $C_7$-$C_{30}$ aryl(alkyl)amino or salt thereof, $C_7$-$C_{30}$ di(arylalkyl)amino or salt thereof, $C_8$-$C_{30}$ alkyl(arylalkyl)amino or salt thereof, $C_{15}$-$C_{30}$ aryl(arylalkyl) amino or salt thereof, $C_8$-$C_{30}$ alkenyl(aryl)amino or salt thereof, $C_8$-$C_{30}$ alkynyl(aryl)amino or salt thereof, $C(O)NH_2$ (amido), $C_2$-$C_{30}$ alkylamido, $C_7$-$C_{14}$ arylamido, $C_8$-$C_{30}$ (arylalkyl)amido, $C_2$-$C_{30}$ dialkylamido, $C_{12}$-$C_{28}$ diarylamido, $C_8$-$C_{30}$ aryl(alkyl)amido, $C_{15}$-$C_{30}$ di(arylalkyl)amido, $C_9$-$C_{30}$ alkyl(arylalkyl)amido, $C_{16}$-$C_{30}$ aryl(arylalkyl)amido, thiol, $C_1$-$C_{30}$ alkyhydroxy, $C_6$-$C_{14}$ arylhydroxy, $C_7$-$C_{30}$ arylalkylhydroxy, $C_3$-$C_{30}$ alkenylhydroxy, $C_3$-$C_{30}$ alkynylhydroxy, $C_8$-$C_{30}$ arylalkenylhydroxy, $C_8$-$C_{30}$ arylalkynylhydroxy, $C_3$-$C_{30}$ polyether, $C_3$-$C_{30}$ polyetherester, $C_3$-$C_{30}$ polyester, $C_3$-$C_{30}$ polyamino, $C_3$-$C_{30}$ polyaminoamido, $C_3$-$C_{30}$ polyaminoether, $C_3$-$C_{30}$ polyaminoester, $C_3$-$C_{30}$ polyamidoester, $C_1$-$C_{30}$ alkylthio, $C_6$-$C_{14}$ arylthio, $C_7$-$C_{30}$ arylalkylthio, $C_2$-$C_{30}$ alkenylthio, $C_2$-$C_{30}$ alkynylthio, $C_8$-$C_{30}$ arylalkenylthio, $C_8$-$C_{30}$ arylalkynylthio, $S(O)_2OH$ or salt thereof, or $OP(O)(OH)_2$ or salt thereof; and Z is H, Cl, Br, I, triflate or other pseudohalogen, $B(OH)_2$, $B(OR'')_2$ where R'' is $C_1$-$C_6$ alkyl, 4,4,5,5-tetramethylborolan-2-yl, 5,5-dimethylborinan-2-yl, $R''_3Sn$ where R'' is $C_1$-$C_6$ alkyl, MgCl, MgBr, MgI, $(R''O)_3Si$ where R'' is $C_1$-$C_2$ alkyl, $R''_3Si$ where R'' is independently methyl or benzyl, $R''_{3-x}(R''O)_xSi$ where R'' are independently $C_1$-$C_6$ alkyl, $Me_{3-x}F_xSi$ where x is 1 to 3, ZnCl, ZnBr, ZnI, or any other reactive functionality that can be used for a condensation or addition polymerization or copolymerization to a conjugated polymer, where the C—Z bond is broken and a C—C bond is formed between a Ge comprising fused ring heterocycle unit and a second Ge comprising fused ring heterocycle unit or another conjugated unit. For example, the Z group can be one that is a functionality that is used in: Suzuki coupling; Stille coupling; Kumada coupling; Hiyama coupling; Negishi coupling; Yammamoto nickel mediated homocoupling; oxidative polymerization where oxidants include Fe (III) compounds, $NO^+$ salts, and other agents with reduction potentials greater than the oxidation potential of the DTG containing monomer; or any other polymerization method. In embodiments of the invention, the Z group is a portion of a polymeric chain bonded to the Ge comprising fused ring heterocycle repeating unit, where that portion can be as little as an end capping atom, for example a H atom, or as much as all other repeating units of a homopolymer or copolymer.

In an embodiment of the invention the Ge comprising fused ring heterocycle units can have the structure:

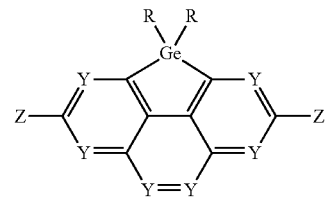

where: Y is CR', N, or P, and where at least one Y is not or CR'; R is independently substituted or unsubstituted $C_1$-$C_{30}$ alkyl, $C_2$-$C_{30}$ alkenyl, $C_2$-$C_{30}$ alkynyl, $C_6$-$C_{14}$ aryl, $C_7$-$C_{30}$ arylalkyl, $C_8$-$C_{30}$ arylalkenyl, $C_8$-$C_{30}$ arylalkynyl, $C_1$-$C_{30}$ alkoxy, $C_6$-$C_{14}$ aryloxy, $C_7$-$C_{30}$ arylalkyloxy, $C_2$-$C_{30}$ alkenyloxy, $C_2$-$C_{30}$ alkynyloxy, $C_8$-$C_{30}$ arylalkenyloxy, $C_8$-$C_{30}$ arylalkynyloxy, $C_1$-$C_{30}$ alkylamino, $C_6$-$C_{14}$ arylamino, $C_7$-$C_{30}$ (arylalkyl)amino, $C_2$-$C_{30}$ alkenylamino, $C_2$-$C_{30}$ alkynylamino, $C_8$-$C_{30}$ (arylalkenyl)amino, $C_8$-$C_{30}$ (arylalkynyl) amino, $C_2$-$C_{30}$ dialkylamino, $C_{12}$-$C_{28}$ diarylamino, $C_4$-$C_{30}$ dialkenylamino, $C_4$-$C_{30}$ dialkynylamino, $C_7$-$C_{30}$ aryl(alkyl) amino, $C_7$-$C_{30}$ di(arylalkyl)amino, $C_8$-$C_{30}$ alkyl(arylalkyl) amino, $C_{15}$-$C_{30}$ aryl(arylalkyl)amino, $C_8$-$C_{30}$ alkenyl(aryl) amino, $C_8$-$C_{30}$ alkynyl(aryl)amino, $C_1$-$C_{30}$ alkylthio, $C_6$-$C_{14}$ arylthio, $C_7$-$C_{30}$ arylalkylthio, $C_2$-$C_{30}$ alkenylthio, $C_2$-$C_{30}$ alkynylthio, $C_8$-$C_{30}$ arylalkenylthio, or $C_8$-$C_{30}$ arylalkynylthio, where one or more substituents, R', can be at any carbon of the R group; R' is independently H, $C_1$-$C_{30}$ alkyl, $C_2$-$C_{30}$ alkenyl, $C_2$-$C_{30}$ alkynyl, $C_6$-$C_{14}$ aryl, $C_7$-$C_{30}$ arylalkyl, $C_8$-$C_{30}$ arylalkenyl, $C_8$-$C_{30}$ arylalkynyl, hydroxy, $C_1$-$C_{30}$ alkoxy, $C_6$-$C_{14}$ aryloxy, $C_7$-$C_{30}$ arylalkyloxy, $C_2$-$C_{30}$ alkenyloxy, $C_2$-$C_{30}$ alkynyloxy, $C_8$-$C_{30}$ arylalkenyloxy, $C_8$-$C_{30}$ arylalkynyloxy, $CO_2H$ or salt thereof, $C_2$-$C_{30}$ alkylester, $C_7$-$C_{15}$ arylester, $C_8$-$C_{30}$ alkylarylester, $C_3$-$C_{30}$ alkenylester, $C_3$-$C_{30}$ alkynylester, $NH_2$ or salt thereof, $C_1$-$C_{30}$ alkylamino or salt thereof, $C_6$-$C_{14}$ arylamino or salt thereof, $C_7$-$C_{30}$ (arylalkyl)amino or salt thereof, $C_2$-$C_{30}$ alkenylamino or salt thereof, $C_2$-$C_{30}$ alkynylamino or salt thereof, $C_8$-$C_{30}$ (arylalkenyl)amino or salt thereof, $C_8$-$C_{30}$ (arylalkynyl) amino or salt thereof, $C_2$-$C_{30}$ dialkylamino or salt thereof, $C_{12}$-$C_{28}$ diarylamino or salt thereof, $C_4$-$C_{30}$ dialkenylamino or salt thereof, $C_4$-$C_{30}$ dialkynylamino or salt thereof, $C_7$-$C_{30}$ aryl(alkyl)amino or salt thereof, $C_7$-$C_{30}$ di(arylalkyl)amino or salt thereof, $C_8$-$C_{30}$ alkyl(arylalkyl)amino or salt thereof, $C_{15}$-$C_{30}$ aryl(arylalkyl)amino or salt thereof, $C_8$-$C_{30}$ alkenyl (aryl)amino or salt thereof, $C_8$-$C_{30}$ alkynyl(aryl)amino or salt thereof, C(O)NH$_2$ (amido), C$_2$-C$_{30}$ alkylamido, C$_7$-C$_{14}$ arylamido, C$_8$-C$_{30}$ (arylalkyl)amido, C$_2$-C$_{30}$ dialkylamido, C$_{12}$-C$_{28}$ diarylamido, C$_8$-C$_{30}$ aryl(alkyl)amido, C$_{15}$-C$_{30}$ di(arylalkyl)amido, C$_9$-C$_{30}$ alkyl(arylalkyl)amido, C$_{16}$-C$_{30}$ aryl(arylalkyl)amido, thiol, C$_1$-C$_{30}$ alkyhydroxy, C$_6$-C$_{14}$ arylhydroxy, C$_7$-C$_{30}$ arylalkylhydroxy, C$_3$-C$_{30}$ alkenylhydroxy, C$_3$-C$_{30}$ alkynylhydroxy, C$_8$-C$_{30}$ arylalkenylhydroxy, C$_8$-C$_{30}$ arylalkynylhydroxy, C$_3$-C$_{30}$ polyether, C$_3$-C$_{30}$ polyetherester, C$_3$-C$_{30}$ polyester, C$_3$-C$_{30}$ polyamino, C$_3$-C$_{30}$ polyaminoamido, C$_3$-C$_{30}$ polyaminoether, C$_3$-C$_{30}$ polyaminoester, C$_3$-C$_{30}$ polyamidoester, C$_1$-C$_{30}$ alkylthio, C$_6$-C$_{14}$ arylthio, C$_7$-C$_{30}$ arylalkylthio, C$_2$-C$_{30}$ alkenylthio, C$_2$-C$_{30}$ alkynylthio, C$_8$-C$_{30}$ arylalkenylthio, C$_8$-C$_{30}$ arylalkynylthio, S(O)$_2$OH or salt thereof, or OP(O)(OH)$_2$ or salt thereof; and Z is H, Cl, Br, I, triflate or other pseudohalogen, B(OH)$_2$, B(OR")$_2$ where R" is C$_1$-C$_6$ alkyl, 4,4,5,5-tetramethylborolan-2-yl, 5,5-dimethylborinan-2-yl, R"$_3$Sn where R" is C$_1$-C$_6$ alkyl, MgCl, MgBr, MgI, (R"O)$_3$Si where R" is C$_1$-C$_2$ alkyl, R"$_3$Si where R" is independently methyl or benzyl, R"$_{3-x}$(R"O)$_x$Si where R" are independently C$_1$—C$_6$ alkyl, Me$_{3-x}$F$_x$Si where x is 1 to 3, ZnCl, ZnBr, ZnI, or any other reactive functionality that can be used for a condensation or addition polymerization or copolymerization to a conjugated polymer, where the C—Z bond is broken and a C—C bond is formed between a Ge comprising fused ring heterocycle unit and a second Ge comprising fused ring heterocycle unit or another conjugated unit. For example, the Z group can be one that is a functionality that is used in: Suzuki coupling; Stille coupling; Kumada coupling; Hiyama coupling; Negishi coupling; Yammamoto nickel mediated homocoupling; oxidative polymerization where oxidants include Fe (III) compounds, NO$^+$ salts, and other agents with reduction potentials greater than the oxidation potential of the DTG containing monomer; or any other polymerization method. In embodiments of the invention, the Z group is a portion of a polymeric chain bonded to the Ge comprising fused ring heterocycle repeating unit, where that portion can be as little as an end capping atom, for example a H atom, or as much as all other repeating units of a homopolymer or copolymer.

In an embodiment of the invention the Ge comprising fused ring heterocycle units can have the structure:

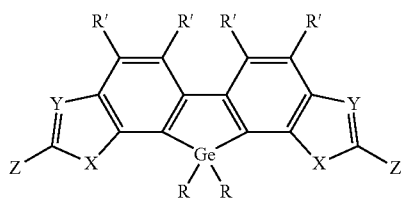

where: X is independently CR'$_2$, SiR'$_2$, PR', P(O)R', O, S, SO, SO$_2$, Se, SeO, SeO$_2$, Te, TeO, or TeO$_2$; Y is CR', N, or P, and where at least one of X and Y is not CR'$_2$ or CR'; R is independently substituted or unsubstituted C$_1$-C$_{30}$ alkyl, C$_2$-C$_{30}$ alkenyl, C$_2$-C$_{30}$ alkynyl, C$_6$-C$_{14}$ aryl, C$_7$-C$_{30}$ arylalkyl, C$_8$-C$_{30}$ arylalkenyl, C$_8$-C$_{30}$ arylalkynyl, C$_1$-C$_{30}$ alkoxy, C$_6$-C$_{14}$ aryloxy, C$_7$-C$_{30}$ arylalkyloxy, C$_2$-C$_{30}$ alkenyloxy, C$_2$-C$_{30}$ alkynyloxy, C$_8$-C$_{30}$ arylalkenyloxy, C$_8$-C$_{30}$ arylalkynyloxy, C$_1$-C$_{30}$ alkylamino, C$_6$-C$_{14}$ arylamino, C$_7$-C$_{30}$ (arylalkyl)amino, C$_2$-C$_{30}$ alkenylamino, C$_2$-C$_{30}$ alkynylamino, C$_8$-C$_{30}$ (arylalkenyl)amino, C$_8$-C$_{30}$ (arylalkynyl)amino, C$_2$-C$_{30}$ dialkylamino, C$_{12}$-C$_{28}$ diarylamino, C$_4$-C$_{30}$ dialkenylamino, C$_4$-C$_{30}$ dialkynylamino, C$_7$-C$_{30}$ aryl(alkyl)amino, C$_7$-C$_{30}$ di(arylalkyl)amino, C$_8$-C$_{30}$ alkyl(arylalkyl)amino, C$_{15}$-C$_{30}$ aryl(arylalkyl)amino, C$_8$-C$_{30}$ alkenyl(aryl)amino, C$_8$-C$_{30}$ alkynyl(aryl)amino, C$_1$-C$_{30}$ alkylthio, C$_6$-C$_{14}$ arylthio, C$_7$-C$_{30}$ arylalkylthio, C$_2$-C$_{30}$ alkenylthio, C$_2$-C$_{30}$ alkynylthio, C$_8$-C$_{30}$ arylalkenylthio, or C$_8$-C$_{30}$ arylalkynylthio, where one or more substituents, R', can be at any carbon of the R group; R' is independently H, C$_1$-C$_{30}$ alkyl, C$_2$-C$_{30}$ alkenyl, C$_2$-C$_{30}$ alkynyl, C$_6$-C$_{14}$ aryl, C$_7$-C$_{30}$ arylalkyl, C$_8$-C$_{30}$ arylalkenyl, C$_8$-C$_{30}$ arylalkynyl, hydroxy, C$_1$-C$_{30}$ alkoxy, C$_6$-C$_{14}$ aryloxy, C$_7$-C$_{30}$ arylalkyloxy, C$_2$-C$_{30}$ alkenyloxy, C$_2$-C$_{30}$ alkynyloxy, C$_8$-C$_{30}$ arylalkenyloxy, C$_8$-C$_{30}$ arylalkynyloxy, CO$_2$H or salt thereof, C$_2$-C$_{30}$ alkylester, C$_7$-C$_{15}$ arylester, C$_8$-C$_{30}$ alkylarylester, C$_3$-C$_{30}$ alkenylester, C$_3$-C$_{30}$ alkynylester, NH$_2$ or salt thereof, C$_1$-C$_{30}$ alkylamino or salt thereof, C$_6$-C$_{14}$ arylamino or salt thereof, C$_7$-C$_{30}$ (arylalkyl)amino or salt thereof, C$_2$-C$_{30}$ alkenylamino or salt thereof, C$_2$-C$_{30}$ alkynylamino or salt thereof, C$_8$-C$_{30}$ (arylalkenyl)amino or salt thereof, C$_8$-C$_{30}$ (arylalkynyl)amino or salt thereof, C$_2$-C$_{30}$ dialkylamino or salt thereof, C$_{12}$-C$_{28}$ diarylamino or salt thereof, C$_4$-C$_{30}$ dialkenylamino or salt thereof, C$_4$-C$_{30}$ dialkynylamino or salt thereof, C$_7$-C$_{30}$ aryl(alkyl)amino or salt thereof, C$_7$-C$_{30}$ di(arylalkyl)amino or salt thereof, C$_8$-C$_{30}$ alkyl(arylalkyl)amino or salt thereof, C$_{15}$-C$_{30}$ aryl(arylalkyl)amino or salt thereof, C$_8$-C$_{30}$ alkenyl(aryl)amino or salt thereof, C$_8$-C$_{30}$ alkynyl(aryl)amino or salt thereof, C(O)NH$_2$ (amido), C$_2$-C$_{30}$ alkylamido, C$_7$-C$_{14}$ arylamido, C$_8$-C$_{30}$ (arylalkyl)amido, C$_2$-C$_{30}$ dialkylamido, C$_{12}$-C$_{28}$ diarylamido, C$_8$-C$_{30}$ aryl(alkyl)amido, C$_{15}$-C$_{30}$ di(arylalkyl)amido, C$_9$-C$_{30}$ alkyl(arylalkyl)amido, C$_{16}$-C$_{30}$ aryl(arylalkyl)amido, thiol, C$_1$-C$_{30}$ alkyhydroxy, C$_6$-C$_{14}$ arylhydroxy, C$_7$-C$_{30}$ arylalkylhydroxy, C$_3$-C$_{30}$ alkenylhydroxy, C$_3$-C$_{30}$ alkynylhydroxy, C$_8$-C$_{30}$ arylalkenylhydroxy, C$_8$-C$_{30}$ arylalkynylhydroxy, C$_3$-C$_{30}$ polyether, C$_3$-C$_{30}$ polyetherester, C$_3$-C$_{30}$ polyester, C$_3$-C$_{30}$ polyamino, C$_3$-C$_{30}$ polyaminoamido, C$_3$-C$_{30}$ polyaminoether, C$_3$-C$_{30}$ polyaminoester, C$_3$-C$_{30}$ polyamidoester, C$_1$-C$_{30}$ alkylthio, C$_6$-C$_{14}$ arylthio, C$_7$-C$_{30}$ arylalkylthio, C$_2$-C$_{30}$ alkenylthio, C$_2$-C$_{30}$ alkynylthio, C$_8$-C$_{30}$ arylalkenylthio, C$_8$-C$_{30}$ arylalkynylthio, S(O)$_2$OH or salt thereof, or OP(O)(OH)$_2$ or salt thereof; and Z is H, Cl, Br, I, triflate or other pseudohalogen, B(OH)$_2$, B(OR")$_2$ where R" is C$_1$-C$_6$ alkyl, 4,4,5,5-tetramethylborolan-2-yl, 5,5-dimethylborinan-2-yl, R"$_3$Sn where R" is C$_1$-C$_6$ alkyl, MgCl, MgBr, MgI, (R"O)$_3$Si where R" is C$_1$-C$_2$ alkyl, R"$_3$Si where R" is independently methyl or benzyl, R"$_{3-x}$(R"O)$_x$Si where R" are independently C$_1$-C$_6$ alkyl, Me$_{3-x}$F$_x$Si where x is 1 to 3, ZnCl, ZnBr, ZnI, or any other reactive functionality that can be used for a condensation or addition polymerization or copolymerization to a conjugated polymer, where the C—Z bond is broken and a C—C bond is formed between a Ge comprising fused ring heterocycle unit and a second Ge comprising fused ring heterocycle unit or another conjugated unit. For example, the Z group can be one that is a functionality that is used in: Suzuki coupling; Stille coupling; Kumada coupling; Hiyama coupling; Negishi coupling; Yammamoto nickel mediated homocoupling; oxidative polymerization where oxidants include Fe (III) compounds, NO$^+$ salts, and other agents with reduction potentials greater than the oxidation potential of the DTG containing monomer; or any other polymerization method. In embodiments of the invention, the Z group is a portion of a polymeric chain bonded to the Ge comprising fused ring heterocycle repeating unit, where that portion can be as little as an end capping atom, for example a H atom, or as much as all other repeating units of a homopolymer or copolymer.

In an embodiment of the invention the Ge comprising fused ring heterocycle units can have the structure:

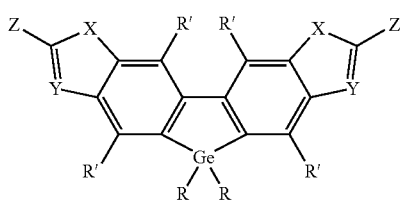

where: X is independently CR'$_2$, SiR'$_2$, PR', P(O)R', O, S, SO, SO$_2$ Se, SeO, SeO$_2$, Te, TeO, or TeO$_2$; Y is CR', N, or P, and where at least one of X and Y is not CR'$_2$ or CR'; R is independently substituted or unsubstituted C$_1$-C$_{30}$ alkyl, C$_2$-C$_{30}$ alkenyl, C$_2$-C$_{30}$ alkynyl, C$_6$-C$_{14}$ aryl, C$_7$-C$_{30}$ arylalkyl, C$_8$-C$_{30}$ arylalkenyl, C$_8$-C$_{30}$ arylalkynyl, C$_1$-C$_{30}$ alkoxy, C$_6$-C$_{14}$ aryloxy, C$_7$-C$_{30}$ arylalkyloxy, C$_2$-C$_{30}$ alkenyloxy, C$_2$-C$_{30}$ alkynyloxy, C$_8$-C$_{30}$ arylalkenyloxy, C$_8$-C$_{30}$ arylalkynyloxy, C$_1$-C$_{30}$ alkylamino, C$_6$-C$_{14}$ arylamino, C$_7$-C$_{30}$ (arylalkyl)amino, C$_2$-C$_{30}$ alkenylamino, C$_2$-C$_{30}$ alkynylamino, C$_8$-C$_{30}$ (arylalkenyl)amino, C$_8$-C$_{30}$ (arylalkynyl)amino, C$_2$-C$_{30}$ dialkylamino, C$_{12}$-C$_{28}$ diarylamino, C$_4$-C$_{30}$ dialkenylamino, C$_4$-C$_{30}$ dialkynylamino, C$_7$-C$_{30}$ aryl(alkyl)amino, C$_7$-C$_{30}$ di(arylalkyl)amino, C$_8$-C$_{30}$ alkyl(arylalkyl)amino, C$_{15}$-C$_{30}$ aryl(arylalkyl)amino, C$_8$-C$_{30}$ alkenyl(aryl)amino, C$_8$-C$_{30}$ alkynyl(aryl)amino, C$_1$-C$_{30}$ alkylthio, C$_6$-C$_{14}$ arylthio, C$_7$-C$_{30}$ arylalkylthio, C$_2$-C$_{30}$ alkenylthio, C$_2$-C$_{30}$ alkynylthio, C$_8$-C$_{30}$ arylalkenylthio, or C$_8$-C$_{30}$ arylalkynylthio, where one or more substituents, R', can be at any carbon of the R group; R' is independently H, C$_1$-C$_{30}$ alkyl, C$_2$-C$_{30}$ alkenyl, C$_2$-C$_{30}$ alkynyl, C$_6$-C$_{14}$ aryl, C$_7$-C$_{30}$ arylalkyl, C$_8$-C$_{30}$ arylalkenyl, C$_8$-C$_{30}$ arylalkynyl, hydroxy, C$_1$-C$_{30}$ alkoxy, C$_6$-C$_{14}$ aryloxy, C$_7$-C$_{30}$ arylalkyloxy, C$_2$-C$_{30}$ alkenyloxy, C$_2$-C$_{30}$ alkynyloxy, C$_8$-C$_{30}$ arylalkenyloxy, C$_8$-C$_{30}$ arylalkynyloxy, CO$_2$H or salt thereof, C$_2$-C$_{30}$ alkylester, C$_7$-C$_{15}$ arylester, C$_8$-C$_{30}$ alkylarylester, C$_3$-C$_{30}$ alkenylester, C$_3$-C$_{30}$ alkynylester, NH$_2$ or salt thereof, C$_1$-C$_{30}$ alkylamino or salt thereof, C$_6$-C$_{14}$ arylamino or salt thereof, C$_7$-C$_{30}$ (arylalkyl)amino or salt thereof, C$_2$-C$_{30}$ alkenylamino or salt thereof, C$_2$-C$_{30}$ alkynylamino or salt thereof, C$_8$-C$_{30}$ (arylalkenyl)amino or salt thereof, C$_8$-C$_{30}$ (arylalkynyl)amino or salt thereof, C$_2$-C$_{30}$ dialkylamino or salt thereof, C$_{12}$-C$_{28}$ diarylamino or salt thereof, C$_4$-C$_{30}$ dialkenylamino or salt thereof, C$_4$-C$_{30}$ dialkynylamino or salt thereof, C$_7$-C$_{30}$ aryl(alkyl)amino or salt thereof, C$_7$-C$_{30}$ di(arylalkyl)amino or salt thereof, C$_8$-C$_{30}$ alkyl(arylalkyl)amino or salt thereof, C$_{15}$-C$_{30}$ aryl(arylalkyl)amino or salt thereof, C$_8$-C$_{30}$ alkenyl(aryl)amino or salt thereof, C$_8$-C$_{30}$ alkynyl(aryl)amino or salt thereof, C(O)NH$_2$ (amido), C$_2$-C$_{30}$ alkylamido, C$_7$-C$_{14}$ arylamido, C$_8$-C$_{30}$ (arylalkyl)amido, C$_2$-C$_{30}$ dialkylamido, C$_{12}$-C$_{28}$ diarylamido, C$_8$-C$_{30}$ aryl(alkyl)amido, C$_{15}$-C$_{30}$ di(arylalkyl)amido, C$_9$-C$_{30}$ alkyl(arylalkyl)amido, C$_{16}$-C$_{30}$ aryl(arylalkyl)amido, thiol, C$_1$-C$_{30}$ alkyhydroxy, C$_6$-C$_{14}$ arylhydroxy, C$_7$-C$_{30}$ arylalkylhydroxy, C$_3$-C$_{30}$ alkenylhydroxy, C$_3$-C$_{30}$ alkynylhydroxy, C$_8$-C$_{30}$ arylalkenylhydroxy, C$_8$-C$_{30}$ arylalkynylhydroxy, C$_3$-C$_{30}$ polyether, C$_3$-C$_{30}$ polyetherester, C$_3$-C$_{30}$ polyester, C$_3$-C$_{30}$ polyamino, C$_3$-C$_{30}$ polyaminoamido, C$_3$-C$_{30}$ polyaminoether, C$_3$-C$_{30}$ polyaminoester, C$_3$-C$_{30}$ polyamidoester, C$_1$-C$_{30}$ alkylthio, C$_6$-C$_{14}$ arylthio, C$_7$-C$_{30}$ arylalkylthio, C$_2$-C$_{30}$ alkenylthio, C$_2$-C$_{30}$ alkynylthio, C$_8$-C$_{30}$ arylalkenylthio, C$_8$-C$_{30}$ arylalkynylthio, S(O)$_2$OH or salt thereof, or OP(O)(OH)$_2$ or salt thereof; and Z is H, Cl, Br, I, triflate or other pseudohalogen, B(OH)$_2$, B(OR")$_2$ where R" is C$_1$-C$_6$ alkyl, 4,4,5,5-tetramethylborolan-2-yl, 5,5-dimethylborinan-2-yl, R"$_3$Sn where R" is C$_1$-C$_6$ alkyl, MgCl, MgBr, MgI, (R"O)$_3$Si where R" is C$_1$-C$_2$ alkyl, R"$_3$Si where R" is independently methyl or benzyl, R"$_{3-x}$ (R"O)$_x$Si where R" are independently C$_1$-C$_6$ alkyl, Me$_{3-x}$F$_x$Si where x is 1 to 3, ZnCl, ZnBr, ZnI, or any other reactive functionality that can be used for a condensation or addition polymerization or copolymerization to a conjugated polymer, where the C—Z bond is broken and a C—C bond is formed between a Ge comprising fused ring heterocycle unit and a second Ge comprising fused ring heterocycle unit or another conjugated unit. For example, the Z group can be one that is a functionality that is used in: Suzuki coupling; Stille coupling; Kumada coupling; Hiyama coupling; Negishi coupling; Yammamoto nickel mediated homocoupling; oxidative polymerization where oxidants include Fe (III) compounds, NO$^+$ salts, and other agents with reduction potentials greater than the oxidation potential of the DTG containing monomer; or any other polymerization method. In embodiments of the invention, the Z group is a portion of a polymeric chain bonded to the Ge comprising fused ring heterocycle repeating unit, where that portion can be as little as an end capping atom, for example a H atom, or as much as all other repeating units of a homopolymer or copolymer.

In embodiments of the invention, homopolymers can be prepared by any condensation method where the same Ge comprising fused ring heterocyclic unit has either self-condensable groups Zs, such as H or halogen, or where two monomers having like Ge comprising fused ring heterocyclic units but have complementary condensable Z groups are combined to yield a desired polymer upon carrying out the polymerization reaction. The proportion of the two monomers can be equal or unequal such that the molecular weight can be the largest possible or be a desired smaller size, respectively. The homopolymer can be capped by a desired end unit, where a monofunctional unit contains a reactive Z unit. The end-capping units can be difunctional units, including end-functional polymers, such that the homopolymers can be linked by the difunctional units, for example as block copolymers. The end-capping units can be difunctional units, including end-functional polymers, such that the homopolymers can be linked by the difunctional units, for example as block copolymers. The end-capping units can be multifunctional units, including functionalized polymers, such that the homopolymers can be linked by the multifunctional units, for example as branched or network polymers and copolymers. In embodiments of the invention, the end-capping unit can be a Ge comprising fused ring heterocyclic unit with only one Z unit that is reactive toward the polymerization reaction or one of the CR' or CR'$_2$ units can have an R' unit replaced with an additional reactive Z unit such that it can function as a non-functional unit for control of the degree of polymerization or as a multifunctional unit for the preparation of branched polymers or a network, respectively. Copolymers comprising a plurality of different Ge comprising fused ring heterocyclic units can be prepared where all comonomers have common self-condensable Z groups, or where two complementary condensable Z groups are present. When one Ge comprising fused ring heterocyclic unit has one condensable Z group and a different Ge comprising fused ring heterocyclic unit has the complementary condensable Z group, an alternating copolymer can be formed. Copolymers can be alternating, random, or block copolymers. As with the homopolymers, copolymers can be end-capped with monofunctional, difunctional, or multifunctional units such that molecular weight can be controlled and/or block, branched, or network polymers can be formed.

In embodiments of the invention, copolymers can contain, in addition to one or more Ge comprising fused ring heterocycle units, one or more other conjugated units including, but not limited to, substituted or unsubstituted, ethenylene, ethynylene, phenylene, naphthylene, anthracene, pyrene, N,N' alkyl or aryl napthalenediimides, N,N' alkyl or aryl perylenediimides, silacyclopentadithiophene, benzothiadiazole, thiadiazoloquinoxaline, cyclopentadithiophene, cyclopentadithiophene oxide, benzoisothiazole, benzothiazole, thiophene oxide, thienothiophene, thienothiophene oxide, dithienothiophene, dithienothiophene oxide, tetrahydroisoindole, fluorene, fluorenone, thiazole, thiazolo[5,4-d]thiazole, selenophene, silole, thiazolothiazole, cyclopentadithiazole, naphthothiadiazole, thienopyrazine, oxazole, imidazole, pyrimidine, benzoxazole, phthalimide, N-alkyl or aryl thieno [3,4-c]pyrrolo-4,6-dione, germafluorene, benzimidazole, quinoxaline, benzo[d][1,2,3]triazole, pyrido[3,4-b]pyrazine, cyanovinylene, thiazolo[5,4-d]thiazole, 1,3,4-thiadiazole, pyrrolo[3,4-c]pyrrole-1,4-dione, 2,2'-bithiazole, benzo[c][1, 2,5]thiadiazole, [1,2,5]thiadiazolo[3,4-c]pyridine, thieno[3, 4-b]pyrazine, [1,2,5]oxadiazolo[3,4-c]pyridine, benzo[1,2-c; 4,5-c']bis[1,2,5]thiadiazole, [1,2,5]thiadiazolo[3,4-g] quinoxaline, dicyanovinylene, 4-dicyanomethylenecyclopentadithiolene, benzo[c] thiophene benzo[c][1,2,5]oxadiazole, or any derivative thereof. Oligomers and/or polymers with one or more of these conjugated units can be used as a macromonomer for preparation of a copolymer with one or more Ge comprising fused ring heterocycle units. Oligomers and/or polymers of the Ge comprising fused ring heterocycle units can be used as a macromonomer for preparation of the copolymer with one or more of the conjugated units that are monomeric, oligomeric and/or polymeric. The resulting polymers can be random copolymers, alternating copolymers, or block copolymers. By using monomeric, dimeric or polymeric end-cappers, the molecular weight can be controlled and/or block, branched, or network polymers can be formed.

Figure 2:
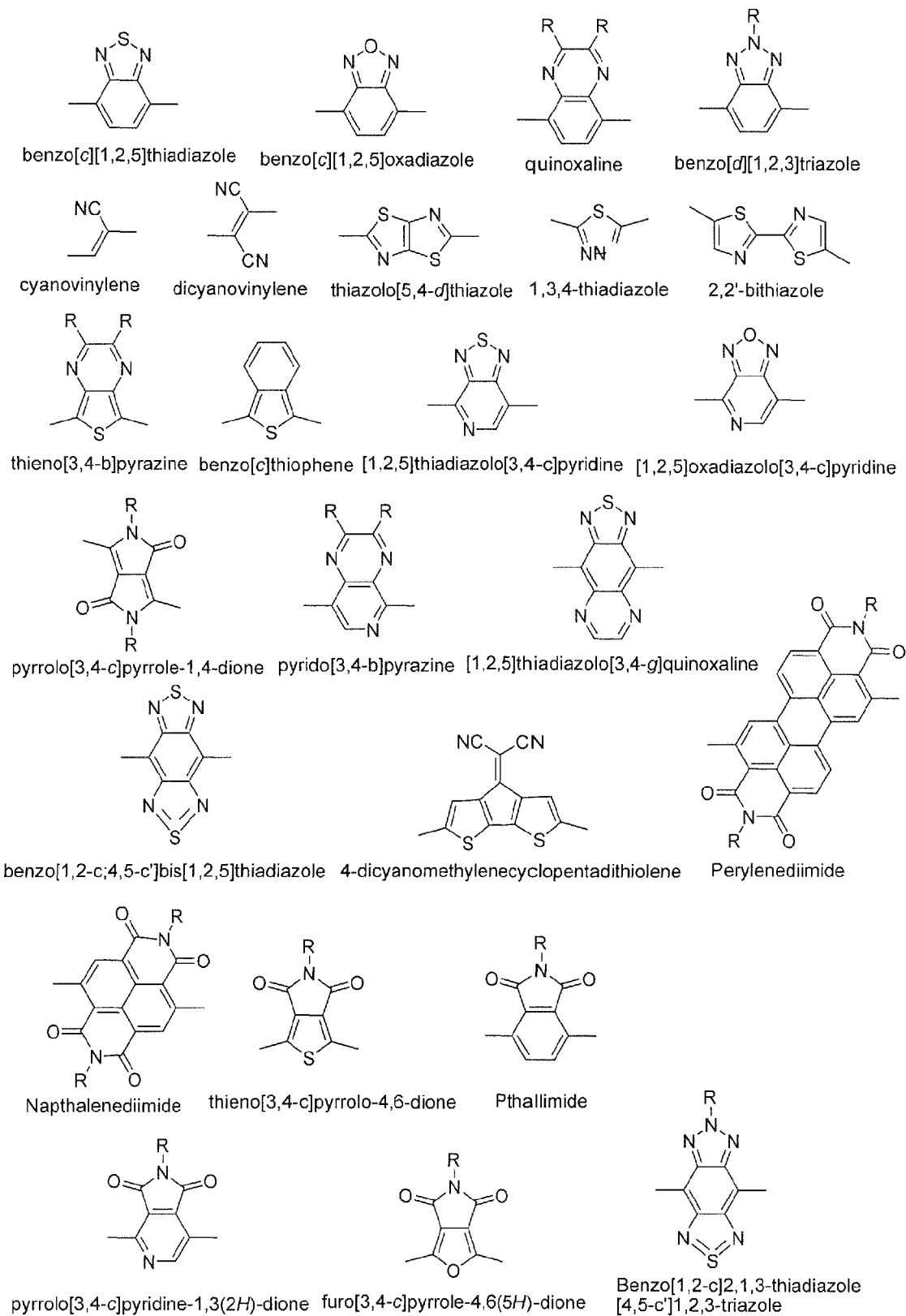
FIG. 2 shows the structure of acceptor units that can be used to form donor-acceptor (DA) copolymers with units derived from Ge comprising fused ring heterocyclic compounds according to embodiments of the invention.

In embodiments of the invention, one or more Ge comprising fused ring heterocycle units can be a donor unit that alternates with one or more acceptor units that comprise: N,N' alkyl or aryl napthalenediimides, N,N' alkyl or aryl perylenediimides, benzo[c][1,2,5]thiadiazole, benzo[c][1,2,5]oxadiazole, benzo[d][1,2,3]triazole, pyrido[3,4-b]pyrazine, cyanovinylene, thiazolo[5,4-d]thiazole, 1,3,4-thiadiazole, pyrrolo[3,4-c]pyrrole-1,4-dione, 2,2'-bithiazole, [1,2,5]thiadiazolo[3,4-c]pyridine, thieno[3,4-b]pyrazine, [1,2,5]oxadiazolo[3,4-c]pyridine, dicyanovinylene, benzo[1,2-c;4,5-c'] bis[1,2,5]thiadiazole, [1,2,5]thiadiazolo[3,4-g]quinoxaline, [1,2,3]triazolo[4,5-g]quinoxaline, [1,2,3]triazolo[4,5-g]quinoxaline, 6λ4d2-[1,2,3]triazolo-[3,4-f]-2,1,3-benzothiadiazole, quinoxaline, 4-dicyanomethylenecyclopentadithiolene, benzo[c]thiophene, or any derivative thereof. Structures of some acceptor units are shown in FIG. 2. These alternating copolymers can be prepared by any method where the reactive group Z of the donor Ge comprising fused ring heterocycle monomer unit is complementary to the reactive group of the acceptor monomeric unit. Suzuki coupling, Stille coupling, Kumada coupling, Hiyama coupling, Negishi coupling, or any other polymerization method can be used to form these donor-acceptor (DA) copolymers.

Figure 3:
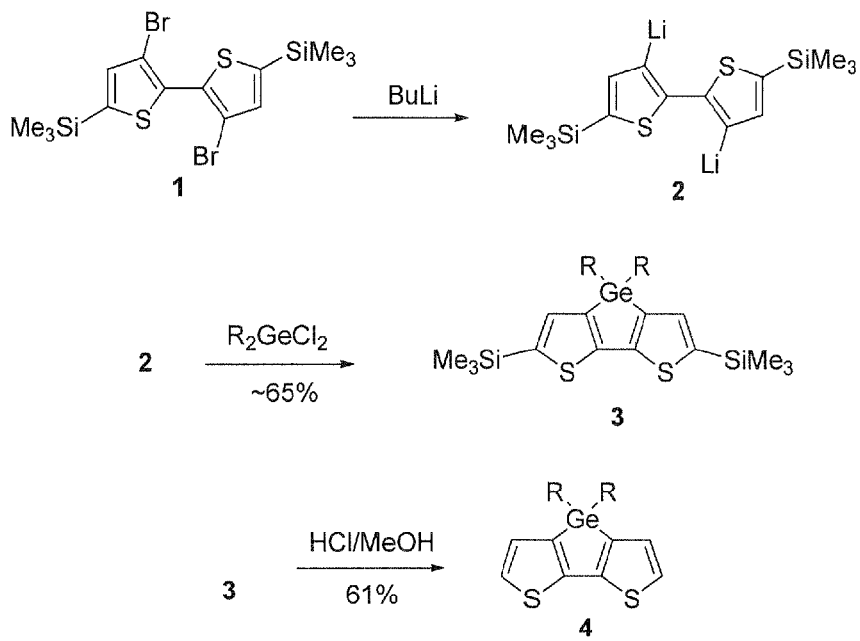
FIG. 3 shows a reaction scheme for the preparation of DTG.
Figure 4:
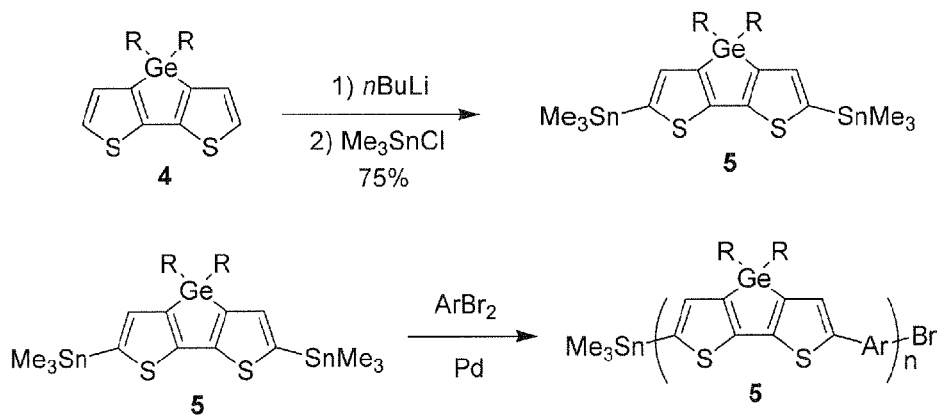
FIG. 4 shows a reaction scheme for the preparation of an alternating copolymer with DTG and aromatic units according to an embodiment of the invention.

For example, DTG can be synthesized as shown by the reaction scheme illustrated in FIG. 3. A dibromobithiophene precursor 1 reacts with butyllithium to give a dilithiated intermediate 2. The intermediate reacts with a diorganodichlorogermane to give product 3 where the organo groups can be alkyl or aryl. Alternatively, precursor 2 reacts with tetrachlorogermane, followed by addition of an organometallic reagent, RM, where M=MgBr, Li, or Cu to yield product 3 where R is an alkyl or aryl group. Removal of the trimethylsilyl protecting groups is accomplished using HCl/MeOH, to give DTG 4. DTG 4 is metallated by reaction with 2 equivalents of alkyllithium followed by quenching with trimethyltin chloride to yield a ditin monomer 5, or halogenated using N-halosuccinimides to give a dihalo monomer as shown in FIG. 4. Ditin monomer 5 reacts with an aryldihalide to give polymer 6 by a Stille condensation, as illustrated in FIG. 4, according to embodiments of the invention.

In embodiments of the invention, the polymers and copolymers contain a sufficient number of R groups, R' groups and/or contain substituents on other conjugated co-units as to render the polymer soluble in a desired solvent. For example, by having all R' groups of a homopolymer with DTG repeating units where all R groups comprising a $C_8$-$C_{12}$ alkyl group, solubility in a hydrocarbon, ether, ketone, ester, or halocarbon comprising solvent can be achieved. As can be appreciated by one skilled in the art, the type and proportion of the R or R' groups or other substituents of a copolymer can be altered to achieve solubility in a desired solvent. Soluble polymers can be used to allow processing the polymers and copolymers according to embodiments of the invention into films or other structures for use as active materials in many applications such as: bulk heterojunction solar cells; bilayer or multilayer solar cells; field effect transistors; diodes and photodiodes; light emitting devices; common photovoltaic devices; antistat conductors and transparent conductors; supercapacitors, batteries, and other energy storage devices; dye sensitized solar cells; electronic paper; and electrochromic windows, displays, and mirrors. These solution processing methods include printing, spraying, and dipping methods.

METHODS AND MATERIALS

2,2'-bistrimethylsilyl-4,4'-bis-(2-ethylhexyl)-dithieno [3,2-b:2',3'-d]germole (3)

To 10 mL of a 2.5 M nBuLi solution in hexanes and 250 mL diethyl ether cooled to −78° C. was added dropwise 5.6 g (12 mmol) of 3,3'-dibromo-2,2'-bithiophene-5,5'-diyl)bis(trimethylsilane) (1) in 30 mL of THF. The resulting solution was stirred for 2.5 h at −78° C. and 4.4 g (12 mmol) of dichlorobis (2-ethylhexyl)germane in 30 mL of diethyl ether was added dropwise. The solution was stirred for 30 min at −78° C., warmed to room temperature, and stirred overnight. The reaction mixture was poured into 0.25 M aq. $NaHCO_3$ and extracted twice with 150 mL of hexanes. The combined organic extract was dried over $MgSO_4$, concentrated by the evaporation of solvents, and chromatographed on silica gel using hexanes as the mobile phase to give 4.3 g (60%) of 3 as a yellow oil. $^1H$ NMR: δ 7.11 (t, J=0.5 Hz, 2H)*, 1.46 (pent, J=6.5 Hz, 2H), 1.34-1.00 (m, 20H), 0.82 (t, J=6.5 Hz, 6H), 0.79 (t, J=7 Hz, 6H), 0.32 (s, 18H). $^{13}C$ NMR: δ 153.0, 146.1, 140.8, 137.0, 37.2, 35.7, 29.2, 29.0, 23.3, 20.8, 14.4, 11.2, 0.4. Elemental Analysis Calc. for $C_{30}H_{54}GeS_2Si_2$: C, 59.28; H, 8.96. Found C, 59.26; H, 8.89. HRMS (ESI) Calc. [M-H$^+$] 609.2495. Found 609.2519.

4,4'-bis-(2-ethylhexyl)-dithieno[3,2-b:2',3'-d] germole (4)

To 4.3 g (7.0 mmol) of 3 in 150 mL of diethyl ether was added 5 mL conc. HCl in 45 mL methanol. The solution was stirred for 1.5 h at room temperature. TLC analysis showed complete consumption of the starting material. The solution was poured into 150 mL of water and extracted twice with 150 mL of hexanes and the combined organic extract was dried over $MgSO_4$ and solvents were evaporated to a residue. The residue was chromatographed on silica gel with a hexanes mobile phase to give 2.0 g (61%) of 4 as a yellow oil. $^1H$ NMR: δ7.19 (d, J=5.0 Hz, 2H)*, 7.03 (d, J=5.0 Hz, 2H), 1.47 (pent, J=6.5 Hz, 2H), 1.34-1.00 (m, 20H), 0.82 (t, J=6.5 Hz, 6H), 0.79 (t, J=7 Hz, 6H). $^{13}$C NMR: δ 146.6, 144.0, 130.0, 124.9, 37.2, 35.7, 29.2, 29.0, 23.3, 20.9, 14.4, 11.1. Elemental Analysis Calc. for $C_{24}H_{38}GeS_2$: C, 62.21; H, 8.27. Found C, 62.27; H, 8.47. HRMS (ESI) Calc. [M-H-]-465.1702. Found 465.1704.

2,2'-bistrimethylstannyl-4,4'-bis-(2-ethylhexyl)-dithieno[3,2-b:2',3'-d]germole (5)

To 2.0 g (4.3 mmol) of 4 in 120 mL THF cooled to −78° C. was added 7 mL of a 2.5 M nBuLi in hexanes (17.4 mmol). The solution was warmed to 0° C. and stirred for 3 hours. The solution was cooled to −78° C. and 4.3 g (21.5 mmol) of trimethyltin chloride was added, the resulting solution was warmed to room temperature, and stirred overnight. This solution was poured into 100 mL water, and extracted twice with 100 mL of hexanes. The combined extract were dried, evaporated, and purified by reverse-phase HPLC to give 2.4 g of 5 as a yellow oil. Elemental Analysis Calc. for $C_{30}H_{54}GeS_2Sn_2$: C, 45.67; H, 6.90. Found C, 45.52; H, 6.93. HRMS (ESI) Calc. [M-H$^+$]789.1009. Found 789.1005.

Poly(5,5'(4,4'-bis-(2-ethylhexyl)-dithieno[3,2-b:2',3'-d]germole)alt-3,6-(N-n-octylpthallimide)) (P1)

A 467.2 mg (0.592 mmol) portion of 5 was weighed and transferred to a 50 mL Schlenke tube with quantitative washing with hexanes. The hexanes were removed in vacuo, and 247.1 mg (0.592 mmol) of 3,6-dibromo-N-n-ocytlpthallimide, 5 mg (0.005 mmol) of (Pd$_2$dba$_3$ and 11 mg, 0.030 mmol of P(o-tol)$_3$ were added to the Schlenke tube. The tube was evacuated and backfilled with argon four times. After degassing by four freeze/pump/thaw cycles, 12 mL of toluene was added to the tube, the mixture was heated to 115° C., and stirred for 5 days. The tube was cooled to 60° C., and diethylammonium diethyldithiocarbamate and 25 mL degassed toluene were added and the mixture stirred for 1 hour. The mixture was transferred by pipette into 300 mL methanol to precipitate the polymer. The polymer was filtered using a cellulose thimble and purified by soxhlet extraction with: methanol for 1 day; acetone for 1 day; hexanes for 4 hours; ethyl acetate for 1 day; and chloroform for 3 hours. The chloroform extract was filtered using a 0.45 µm pore size PTFE syringe filter directly into methanol. The solid was collected and residual solvent removed under vacuum for a period of 1 day to yield an orange solid. GPC: Mn 57.0 kDa, Mw 109 kDa, PDI 1.90. $^1$H NMR: δ 7.94 (s, 2H), 7.82 (s, 2H), 3.72 (br, 2H), 1.71 (br, 2H), 1.60 (br, 2H), 1.4-1.2 (m, 32H) 0.86 (m, 15H) Elemental Analysis Calc. for $C_{40}H_{55}GeNO_2S_2$: C, 66.85; H, 7.71; N, 1.95. Found C, 66.94; H, 7.72; N, 1.83.

Poly(5,5'(4,4'-bis-(2-ethylhexyl)-dithieno[3,2-b:2',3'-d]germole)alt-1,3(5-octyl-4H-thieno[3,4-c]pyrrole-4,6(5H)-dione) (P2)

A 695 mg (0.881 mmol) portion of 5 was weighed and transferred to a 50 mL Schlenke tube with the aid of hexanes washings. The hexanes were removed in vacuo and 373 mg of (0.881 mmol) 1,3-dibromo-5-octyl-4H-thieno[3,4-c]pyrrole-4,6(5H)-dione, 6 mg (0.007 mmol) of Pd$_2$dba$_3$, and 13 mg (0.042 mmol) of P(o-tol)$_3$ were added to the tube. The tube was evacuated and backfilled with argon four times. After being degassed by 4 freeze/pump/thaw cycles, 12 mL of toluene was added to the tube, the mixture was heated to 115° C., stirred for 5 days. The mixture was cooled to 60° C., diethylammonium diethyldithiocarbamate and 25 mL of degassed toluene were added, and the mixture stirred for 1 hour. The mixture was transferred by pipette into 300 mL methanol to precipitate the polymer. The polymer was filtered using a cellulose thimble and purified by soxhlet extraction with: methanol for 1 day; acetone for 1 day; hexanes for 1 day; and chloroform for 3 hours. The chloroform extract was filtered through a 0.45 µm pore size PTFE syringe filter directly into methanol, and 518 mg (81%) of precipitated polymer was collected. Chloroform was added to 330 mg of the polymer and the polymer was precipitated in methanol and filtered using a cellulose thimble. The polymer was extracted (soxhlet) with dichloromethane for 1 day and chloroform for 2 hours. The chloroform soluble fraction was filtered through a 0.45 µm pore size PTFE syringe filter directly into acetone, the solid polymer was collected, and residual solvent was removed from the polymer under vacuum for 1 day to yield 300 mg (90%) of a dark solid. $^1$H NMR: δ 8.46 (br, 1H), 7.4 (br, 2H), 3.72 (br, 2H), 2.04 (br, 2H), 1.8-0.7 (br, 49H). Elemental Analysis Calc. for $C_{38}H_{53}GeNO_2S_3$: C, 62.98; H, 7.37; N, 1.93. Found C, 63.26; H, 7.55; N, 1.85.

Poly(5,5' (4,4'-bis-(2-ethylhexyl)-dithieno[3,2-b:2',3'-d]germole)alt-4,7-(2,1,3-benzothiadiazole)) (P3)

A 822 mg (1.04 mmol) portion of 5 was weighed and transferred to a 50 mL Schlenke tube with the aid of hexanes washings. The hexanes were removed in vacuo and 311 mg (1.05 mmol) of 4,7-dibromo-2,1,3-benzothiadiazole, 7 mg (0.008 mmol) of Pd$_2$dba$_3$, and 16 mg (0.052 mmol) P(o-tol)$_3$ were added to the tube, which was evacuated and backfilled with argon four times. After degassing by 4 freeze/pump/thaw cycles, 30 mL of chlorobenzene was added, the mixture heated to 130° C., and stirred for 5 days. The mixture was cooled to 60° C., diethylammonium diethyldithiocarbamate and 20 mL degassed chlorobenzene were added, and the mixture stirred for 1 hour. The mixture was transferred by pipette into 300 mL methanol to precipitate the polymer. The polymer was filtered using a cellulose thimble and purified by soxhlet extraction with: methanol for 1 day; acetone for 1 day; dichloromethane for 1 day; and chlorobenzene for 1 day. The chlorobenzene solution was concentrated to ~100 mL and heated to boiling. The solution was filtered through a 0.45 µm pore size PTFE syringe filter directly into 400 mL methanol and the precipitated solid was collected. The solid was redissolved in hot chlorobenzene, filtered through a 0.45 µm pore size PTFE syringe filter directly into 600 mL THF, and methanol was added until precipitation occurred (~100 mL). The product was filtered using paper, and redissolved in hot chlorobenzene. The solution was filtered into 600 mL ethyl acetate to give 205 mg (33%) of a dark shiny solid. Elemental Analysis Calc. for $C_{30}H_{38}GeN_2S_3$: C, 60.51; H, 6.43, 4.70. Found C, 60.91; H, 6.70; N, 4.35. The residue remaining after the extractions was dissolved in hot dichlorobenzene and filtered through a 0.45 µm pore size PTFE syringe filter directly into 400 mL methanol to yield 248 mg (40%) of a dark solid. Elemental Analysis Calc. for $C_{30}H_{38}GeN_2S_3$: C, 60.51; H, 6.43, 4.70. Found C, 60.13; H, 6.34; N, 4.59.

Figure 5:
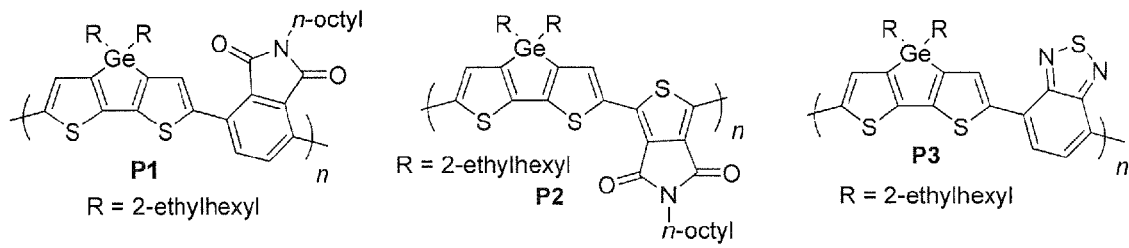
FIG. 5 shows the structures of three alternating copolymers, according to embodiments of the invention.

FIG. 5 shows the structures of polymers P1, P2, and P3. The polymers are high molecular weight; for example, P1 has a $M_n$ of ~65 kDa/mol, and the polymers display colors that are analogous to DTS derivatives.

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

We claim:

1. A polymer, comprising a plurality of Ge comprising heterocyclic repeating units of one or more of the structures:

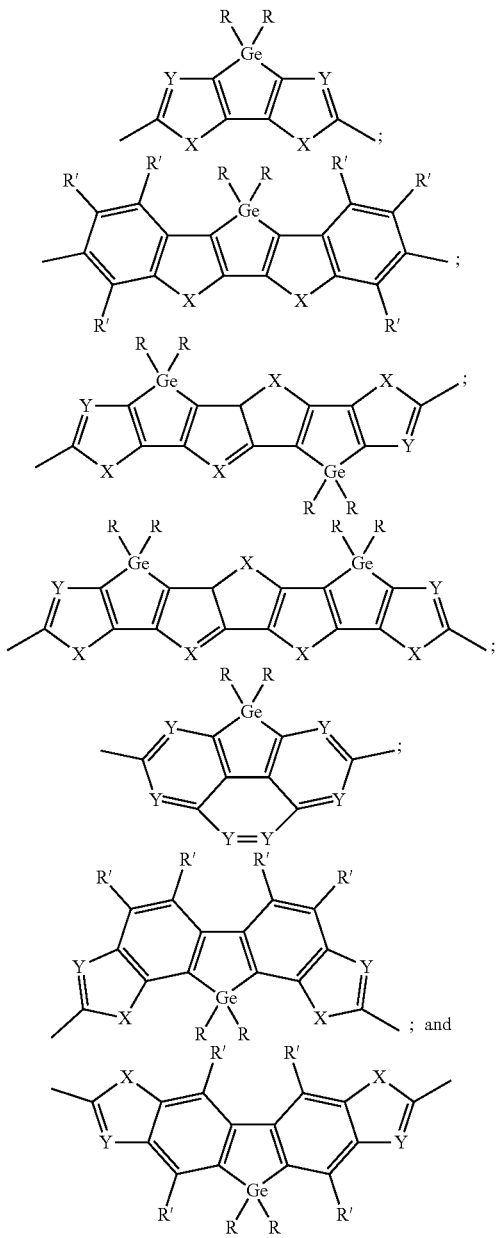

where: X is independently $CR'_2$, $SiR'_2$, $NR'$, $PR'$, $P(O)R'$, $O$, $S$, $SO$, $SO_2$, $Se$, $SeO$, $SeO_2$, $Te$, $TeO$, or $TeO_2$; Y is $CR'$, N, or P, and where at least one of X and Y is not $CR'_2$ or $CR'$; R is independently substituted or unsubstituted $C_1$-$C_{30}$ alkyl, $C_2$-$C_{30}$ alkenyl, $C_2$-$C_{30}$ alkynyl, $C_6$-$C_{14}$ aryl, $C_7$-$C_{30}$ arylalkyl, $C_8$-$C_{30}$ arylalkenyl, or $C_8$-$C_{30}$ arylalkynyl where one or more substituents, R' can be at any carbon of the R group; and R' is independently H, $C_1$-$C_{30}$ alkyl, $C_2$-$C_{30}$ alkenyl, $C_2$-$C_{30}$ alkynyl, $C_6$-$C_{14}$ aryl, $C_7$-$C_{30}$ arylalkyl, $C_8$-$C_{30}$arylalkenyl, $C_8$-$C_{30}$ arylalkynyl, hydroxy, $C_1$-$C_{30}$ alkoxy, $C_6$-$C_{14}$ aryloxy, $C_7$-$C_{30}$arylalkyloxy, $C_2$-$C_{30}$alkenyloxy, $C_2$-$C_{30}$alkynyloxy, $C_8$-$C_{30}$arylalkenyloxy, $C_8$-$C_{30}$arylalkynyloxy, $CO_2H$, $C_2$-$C_{30}$alkylester, $C_7$-$C_{15}$arylester, $C_8$-$C_{30}$alkylarylester, $C_3$-$C_{30}$alkenylester, $C_3$-$C_{30}$ alkynylester, $NH_2$, $C_1$-$C_{30}$ alkylamino, $C_6$-$C_{14}$ arylamino, $C_7$-$C_{30}$ (arylalkyl)amino, $C_2$-$C_{30}$ alkenylamino, $C_2$-$C_{30}$alkynylamino, $C_8$-$C_{30}$(arylalkenyl) amino, $C_8$-$C_{30}$(arylalkynyl)amino, $C_2$-$C_{30}$ dialkylamino, $C_{12}$-$C_{28}$ diarylamino, $C_4$-$C_{30}$ dialkenylamino, $C_4$-$C_{30}$ dialkynylamino, $C_7$-$C_{30}$aryl(alkyl)amino, $C_7$-$C_{30}$ di(arylalkyl) amino, $C_8$-$C_{30}$alkyl(arylalkyl)amino, $C_{15}$-$C_{30}$aryl(arylalkyl) amino, $C_8$-$C_{30}$alkenyl(aryl)amino, $C_8$-$C_{30}$ alkynyl(aryl) amino, $C(O)NH_2$, (amido), $C_2$-$C_{30}$ alkylamido, $C_7$-$C_{14}$ arylamido, $C_8$-$C_{30}$ (arylalkyl)amido, $C_2$-$C_{30}$ dialkylamido, $C_{12}$-$C_{28}$diarylamido, $C_8$-$C_{30}$aryl(alkyl)amido, $C_{15}$-$C_{30}$di (arylalkyl)amido, $C_9$-$C_{30}$alkyl(arylalkyl)amido, $C_{16}$-$C_{30}$aryl (arylalkyl)amido, thiol, $C_1$-$C_{30}$alkyhydroxy, $C_6$-$C_{14}$arylhydroxy, $C_7$-$C_{30}$ arylalkylhydroxy, $C_3$-$C_{30}$ alkenylhydroxy, $C_3$-$C_{30}$alkynylhydroxy, $C_8$-$C_{30}$arylalkenylhydroxy, $C_8$-$C_{30}$ arylalkynylhydroxy, $C_3$-$C_{30}$ polyether, $C_3$-$C_{30}$ polyetherester, $C_3$-$C_{30}$ polyester, $C_3$-$C_{30}$polyamino, $C_3$-$C_{30}$polyaminoamido, $C_3$-$C_{30}$polyaminoether, $C_3$-$C_{30}$polyaminoester, or $C_1$-$C_{30}$polyamidoester.

2. The polymer of claim 1, wherein the polymer is a homopolymer having a plurality of the Ge comprising heterocyclic units of identical structure.

3. The polymer of claim 1, wherein the polymer is a copolymer having a plurality of at least two of the Ge comprising heterocyclic units.

4. The polymer of claim 1, wherein the polymer is a copolymer having a plurality of at least one of the Ge comprising heterocyclic units and at least one conjugated repeating unit comprising a substituted or unsubstituted, ethenylene, ethynylene, phenylene, naphthylene, silacyclopentadithiophene, benzothiadiazole, thiadiazoloquinoxaline, cyclopentadithiophene, cyclopentadithiophene oxide, benzoisothiazole, benzothiazole, thiophene oxide, thienothiophene, thienothiophene oxide, dithienothiophene, dithienothiophene oxide, tetrahydroisoindole, fluorene, fluorenone, thiazole, selenophene, silole, thiazolothiazole, cyclopentadithiazole, naphthothiadiazole, thienopyrazine, oxazole, imidazole, pyrimidine, benzoxazole, phthalimide, 3,4-thiophenedicarboxylic acid imide, germafluorene, benzimidazole, quinoxaline, benzo[d][1,2,3]triazole, pyrido[3,4-b]pyrazine, cyanovinylene, thiazolo[5,4-d]thiazole, 1,3,4-thiadiazole, pyrrolo[3,4-c]pyrrole-1,4-dione, 2,2'-bithiazole, benzo[c][1,2,5]thiadiazole, [1,2,5]thiadiazolo[3,4-c]pyridine, thieno[3,4-b]pyrazine, [1,2,5]oxadiazolo[3,4-c]pyridine, dicyanovinylene, benzo[1,2-c;4,5-c']bis[1,2,5]thiadiazole, [1,2,5]thiadiazolo[3,4-g]quinoxaline, 4-dicyanomethylenecyclopentadithiolene, benzo[c] thiophene benzo[c][1,2,5]oxadiazole, and/or any derivative thereof.

5. The polymer of claim 4, wherein the conjugated repeating units comprises one or more acceptor units.

6. The polymer of claim 5, wherein the acceptor units comprise thieno[3,4-c]pyrrolo-4,6-dione, benzo[c][1,2,5] thiadiazole, benzo[c][1,2,5]oxadiazole, benzo[d][1,2,3]triazole, pyrido[3,4-b]pyrazine, cyanovinylene, thiazolo[5,4-d] thiazole, 1,3,4-thiadiazole, pyrrolo[3,4-c]pyrrole-1,4-dione, 2,2'-bithiazole, [1,2,5]thiadiazolo[3,4-c]pyridine, thieno[3, 4-b]pyrazine, [1,2,5]oxadiazolo[3,4-c]pyridine, dicyanovinylene, benzo[1,2-c;4,5-c']bis[1,2,5]thiadiazole, [1,2,5]thiadiazolo[3,4-g]quinoxaline, quinoxaline, 4-dicyanomethylenecyclopentadithiolene, benzo[c]thiophene or any derivative thereof.

7. A method of preparing a polymer of claim 1, comprising performing a Suzuki coupling, Stille coupling, Kumada coupling, Hiyama coupling, or Negishi coupling reaction with at least one monomer of the Ge comprising heterocyclic compound of a)
b)
c)
d)
e)
f)
g)

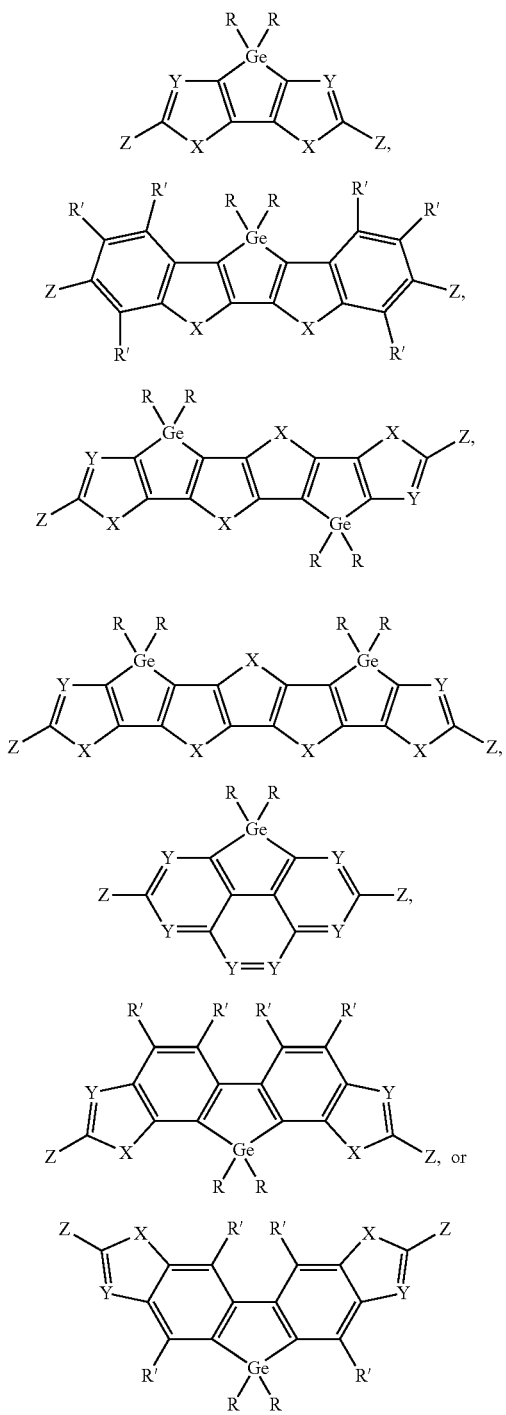

where: X is independently $CR'_2$, $SiR'_2$, $NR'$, $PR'$, $P(O)R'$, O, S, SO, $SO_2$ Se, SeO, $SeO_2$, Te, TeO, or $TeO_2$; Y is $CR'$, N, or P, and where at least one of X and Y is not $CR'_2$ or $CR'$; R is independently substituted or unsubstituted $C_1$-$C_{30}$ alkyl, $C_2$-$C_{30}$ alkenyl, $C_2$-$C_{30}$ alkynyl, $C_6$-$C_{14}$ aryl, $C_7$-$C_{30}$ arylalkyl, $C_8$-$C_{30}$ arylalkenyl, or $C_8$-$C_{30}$ arylalkynyl where one or more substituents, R', can be at any carbon of the R group; R' is independently H, $C_1$-$C_{30}$ alkyl, $C_2$-$C_{30}$ alkenyl, $C_2$-$C_{30}$ alkynyl, $C_6$-$C_{14}$ aryl, $C_7$-$C_{30}$ arylalkyl, $C_8$-$C_{30}$ arylalkenyl, $C_8$-$C_{30}$ arylalkynyl, hydroxy, $C_1$-$C_{30}$ alkoxy, $C_6$-$C_{14}$ aryloxy, $C_7$-$C_{30}$ arylalkyloxy, $C_2$-$C_{30}$ alkenyloxy, $C_2$-$C_{30}$ alkynyloxy, $C_8$-$C_{30}$ arylalkenyloxy, $C_8$-$C_{30}$ arylalkynyloxy, $CO_2H$, $C_2$-$C_{30}$ alkylester, $C_7$-$C_{15}$ arylester, $C_8$-$C_{30}$ alkylarylester, $C_3$-$C_{30}$ alkenylester, $C_3$-$C_{30}$ alkynylester, $NH_2$, $C_1$-$C_{30}$ alkylamino, $C_6$-$C_{14}$ arylamino, $C_7$-$C_{30}$ (arylalkyl)amino, $C_2$-$C_{30}$ alkenylamino, $C_2$-$C_{30}$ alkynylamino, $C_8$-$C_{30}$ (arylalkenyl)amino, $C_8$-$C_{30}$ (arylalkynyl)amino, $C_2$-$C_{30}$ dialkylamino, $C_{12}$-$C_{28}$ diarylamino, $C_4$-$C_{30}$ dialkenylamino, $C_4$-$C_{30}$ dialkynylamino, $C_7$-$C_{30}$ aryl(alkyl)amino, $C_7$-$C_{30}$ di(arylalkyl)amino, $C_8$-$C_{30}$ alkyl(arylalkyl)amino, $C_{15}$-$C_{30}$ aryl(arylalkyl)amino, $C_8$-$C_{30}$ alkenyl(aryl)amino, $C_8$-$C_{30}$ alkynyl(aryl)amino, $C(O)NH_2$ (amido), $C_2$-$C_{30}$ alkylamido, $C_7$-$C_{14}$ arylamido, $C_8$-$C_{30}$ (arylalkyl)amido, $C_2$-$C_{30}$ dialkylamido, $C_{12}$-$C_{28}$ diarylamido, $C_8$-$C_{30}$ aryl(alkyl)amido, $C_{15}$-$C_{30}$ di(arylalkyl)amido, $C_9$-$C_{30}$ alkyl(arylalkyl)amido, $C_{16}$-$C_{30}$ aryl(arylalkyl)amido, thiol, $C_1$-$C_{30}$ alkylhydroxy, $C_6$-$C_{14}$ arylhydroxy, $C_7$-$C_{30}$ arylalkylhydroxy, $C_3$-$C_{30}$ alkenyl hydroxy, $C_3$-$C_{30}$ alkynyl hydroxy, $C_8$-$C_{30}$ arylalkenyl hydroxy, $C_8$-$C_{30}$ arylalkynylhydroxy, $C_3$-$C_{30}$ polyether, $C_3$-$C_{30}$ polyetherester, $C_3$-$C_{30}$ polyester, $C_3$-$C_{30}$ polyamino, $C_3$-$C_{30}$ polyaminoamido, $C_3$-$C_{30}$ polyaminoether, $C_3$-$C_{30}$ polyaminoester, or $C_3$-$C_{30}$ polyamidoester; and Z is H, Cl, Br, I, triflate, $B(OH)_2$, 4,4,5,5-tetramethylborolan-2-yl, 5,5-dimethylborinan-2-yl, $R''_3Sn$ where R'' is $C_1$-$C_6$ alkyl, MgCl, MgBr, MgI, $(R''O)_3Si$ where R'' is $C_1$-$C_2$ alkyl, $R''_3Si$ where R'' is independently methyl or benzyl, $Me_{3-x}F_xSi$, ZnCl, ZnBr, or ZnI.

8. An electrical device comprising the Ge comprising the polymer of claim 1.

9. The electrical device of claim 8, wherein the device is a bulk heterojunction solar cell, bilayer solar cell, multilayer solar cell, field effect transistor, diode, photodiode, light emitting device (LED), photovoltaic device, anti-stat conductor, transparent conductor, supercapacitor, battery, dye sensitized solar cell, electronic paper, electrochromic window, electrochromic display, or electrochromic mirror.

10. The electrical device of claim 8, wherein the device is a bulk heterojunction solar cell.

11. The electrical device of claim 10, wherein the device further comprises an indium-tin-oxide conductor on a glass substrate, an electron transport layer comprising electron transporting metal oxide nanoparticles or a sol-gel layer, a bulk heterojunction layer comprising the polymer of claim 2 and a fullerene derivative, and a hole extraction electrode comprising a metal oxide/metal layer.

12. The electrical device of claim 11, wherein the electron transport layer comprises a layer of ZnO nanoparticles, a ZnO sol-gel film, $TiO_2$ nanoparticles or a $TiO_2$ sol-gel film.

13. The electrical device of claim 11, wherein the metal oxide/metal layer comprises $MoO_3$/silver, $MoO_3$/aluminum, $WO_3$/silver, $WO_3$/aluminum layer.

* * * * *

UNITED STATES PATENT AND TRADEMARK OFFICE
CERTIFICATE OF CORRECTION

PATENT NO. : 9,006,376 B2
APPLICATION NO. : 14/001787
DATED : April 14, 2015
INVENTOR(S) : Chad Martin Amb, Franky So and John R. Reynolds It is certified that error appears in the above-identified patent and that said Letters Patent is hereby corrected as shown below:

In the specification

Column 1,
Line 58, "solar cells" should read --solar cells.--.

Column 7,
Lines 27-28, "or $C_8$-$C_3$ arylalkynylthio" should read --or $C_8$-$C_{30}$ arylalkynylthio--.

Column 11,
Lines 9-10, "Y is not or CR'; and" should read --Y is not CR'; and--.

Column 12,
Lines 32-33, "Y is not or CR'; R" should read --Y is not CR'; R--.

Column 18,
Line 60, "5 mL cone." should read --Found C--.

Column 19,
Line 5, "Found C," should read --Found C--.
Line 6, "[M-H$^+$]-465.1702. Found" should read --[M-H$^+$] 465.1702, Found--.

In the claims

Column 24,
Line 54, "of claim 2" should read --of claim 1--.

Signed and Sealed this
Eighth Day of December, 2015

Michelle K. Lee
*Director of the United States Patent and Trademark Office*